(12) United States Patent
Destaillats et al.

(10) Patent No.: US 10,820,616 B2
(45) Date of Patent: Nov. 3, 2020

(54) INFANT FORMULA SYSTEM WITH ADAPTIVE LEVELS OF HUMAN MILK OLIGOSACCHARIDES (HMOS)

(71) Applicant: NESTEC S.A., Vevey (CH)

(72) Inventors: Frederic Destaillats, Servion (CH); Carlos Antonio De Castro, Geneva (CH); Norbert Sprenger, Savigny (CH); Sagar Thakkar, Brent (CH); Sean Christopher Austin, Mezieres (CH)

(73) Assignee: Societe des Produits Nestle S.A., Vevey (CH)

( * ) Notice: Subject to any disclaimer, the term of this patent is extended or adjusted under 35 U.S.C. 154(b) by 492 days.

(21) Appl. No.: 15/514,145

(22) PCT Filed: Sep. 24, 2015

(86) PCT No.: PCT/EP2015/071930
§ 371 (c)(1),
(2) Date: Mar. 24, 2017

(87) PCT Pub. No.: WO2016/046294
PCT Pub. Date: Mar. 31, 2016

(65) Prior Publication Data
US 2017/0295838 A1    Oct. 19, 2017

(30) Foreign Application Priority Data

Sep. 25, 2014 (EP) .................................. 14186352
Mar. 18, 2015 (EP) .................................. 15159584

(51) Int. Cl.
*A23L 33/125* (2016.01)
*A23L 33/00* (2016.01)
*A61K 9/00* (2006.01)
*A61K 31/702* (2006.01)

(52) U.S. Cl.
CPC ............. *A23L 33/125* (2016.08); *A23L 33/30* (2016.08); *A23L 33/40* (2016.08); *A61K 9/0095* (2013.01); *A61K 31/702* (2013.01); *A23V 2002/00* (2013.01)

(58) Field of Classification Search
None
See application file for complete search history.

(56) References Cited

U.S. PATENT DOCUMENTS 6,146,670 A    11/2000   Prieto et al.

FOREIGN PATENT DOCUMENTS

| EP | 2656862 | | 10/2013 | |
| RU | 2508743 | C2 | 3/2014 | |
| WO | 2009068549 | | 6/2009 | |
| WO | 2011051482 | | 5/2011 | |
| WO | WO-2012156273 | A1 * | 11/2012 | ............... C07H 5/06 |
| WO | 2013025104 | | 2/2013 | |
| WO | 2013032674 | | 3/2013 | |
| WO | 2014070016 | | 5/2014 | |

OTHER PUBLICATIONS

Xu et al. 'Breastfeeding in China.' Int. Biofeed. J. 4:6, 1-15, 2009.*
Austin et al. 'Temporal Change of the Content of 10 Oligosaccharides in the Milk of Chinese Urban Mothers.' Nutrients 2016, 8, 346; doi:10.3390/nu8060346.*
Gridneva et al. 'Human Milk Casein and Whey Protein and Infant Body Composition over the First 12 Months of Lactation.' Nutrients 2018, 10, 1332; doi:10.3390/nu10091332.*

* cited by examiner

Primary Examiner — Nora M Rooney
(74) Attorney, Agent, or Firm — K&L Gates LLP

(57) ABSTRACT

This invention relates to an age-tailored nutritional composition system comprising an adaptive level of human milk oligosaccharides (HMOS) and a method for preparing said system. The age-tailored nutritional composition system comprises at least two nutritional compositions for infants of a certain age, which differ from each other in the amount of HMOs present therein. It is specifically adapted to the evolving nutritional needs of infants from their birth to the end of the breast feeding period.

15 Claims, 3 Drawing Sheets

| Unit | Visit | Female | | | | | Male | | | | | Combined | | | | |
|---|---|---|---|---|---|---|---|---|---|---|---|---|---|---|---|---|
| | | N | Min | Mean | SD | Max | N | Min | Mean | SD | Max | N | Min | Mean | SD | Max |
| mg per L | V1 | 25 | 6.68 | 1516.92 | 1326.91 | 4990.30 | 25 | 9.27 | 1451.30 | 1127.52 | 3579.36 | 50 | 6.68 | 1484.11 | 1219.08 | 4990.30 |
| | V2 | 25 | 9.50 | 1209.98 | 1045.97 | 3863.08 | 25 | 6.48 | 1201.27 | 917.08 | 2836.09 | 50 | 6.48 | 1205.62 | 973.56 | 3863.08 |
| | V3 | 23 | 4.58 | 924.22 | 836.22 | 3505.37 | 25 | 4.47 | 972.52 | 792.92 | 2634.61 | 48 | 4.47 | 949.37 | 805.58 | 3505.37 |

FIG. 2

| Unit | Visit | Female | | | | | Male | | | | | Combined | | | | |
|---|---|---|---|---|---|---|---|---|---|---|---|---|---|---|---|---|
| | | N | Min | Mean | SD | Max | N | Min | Mean | SD | Max | N | Min | Mean | SD | Max |
| mg per L | V1 | 25 | 116.37 | 225.46 | 73.54 | 427.15 | 25 | 82.84 | 235.53 | 87.53 | 436.62 | 50 | 82.84 | 230.50 | 80.17 | 436.62 |
| | V2 | 25 | 103.69 | 221.68 | 84.92 | 477.49 | 25 | 86.63 | 199.35 | 56.19 | 320.57 | 50 | 86.63 | 210.51 | 72.15 | 477.49 |
| | V3 | 24 | 26.09 | 208.38 | 88.96 | 461.97 | 25 | 107.58 | 202.19 | 47.77 | 295.19 | 49 | 26.09 | 205.22 | 70.31 | 461.97 |

FIG. 3

| Unit | Visit | Female | | | | | Male | | | | | Combined | | | | |
|---|---|---|---|---|---|---|---|---|---|---|---|---|---|---|---|---|
| | | N | Min | Mean | SD | Max | N | Min | Mean | SD | Max | N | Min | Mean | SD | Max |
| mg per L | V1 | 25 | 129.54 | 255.00 | 109.83 | 533.52 | 25 | 63.61 | 223.34 | 79.56 | 378.10 | 50 | 63.61 | 239.17 | 96.25 | 533.52 |
| | V2 | 25 | 58.78 | 162.26 | 71.97 | 397.30 | 25 | 39.23 | 133.57 | 66.54 | 282.90 | 50 | 39.23 | 147.92 | 70.11 | 397.30 |
| | V3 | 23 | 31.99 | 110.32 | 72.67 | 352.57 | 25 | 16.41 | 80.98 | 64.63 | 301.70 | 48 | 16.41 | 95.04 | 69.46 | 352.57 |

FIG. 4

| Unit | Visit | Female | | | | | Male | | | | | Combined | | | | |
|---|---|---|---|---|---|---|---|---|---|---|---|---|---|---|---|---|
| | | N | Min | Mean | SD | Max | N | Min | Mean | SD | Max | N | Min | Mean | SD | Max |
| mg per L | V1 | 25 | 208.40 | 531.77 | 187.17 | 889.43 | 25 | 240.20 | 549.17 | 167.41 | 1000.40 | 50 | 208.40 | 540.47 | 175.96 | 1000.40 |
| | V2 | 25 | 68.00 | 274.96 | 121.16 | 578.65 | 25 | 124.85 | 275.29 | 98.07 | 478.45 | 50 | 68.00 | 275.13 | 109.09 | 578.65 |
| | V3 | 23 | 58.56 | 127.41 | 63.00 | 339.95 | 25 | 46.18 | 131.76 | 48.77 | 216.69 | 48 | 46.18 | 129.68 | 55.48 | 339.95 |

FIG. 5

| Unit | Visit | Female | | | | | Male | | | | | Combined | | | | |
|---|---|---|---|---|---|---|---|---|---|---|---|---|---|---|---|---|
| | | N | Min | Mean | SD | Max | N | Min | Mean | SD | Max | N | Min | Mean | SD | Max |
| mg per L | V1 | 25 | 389.80 | 1061.18 | 422.77 | 2041.02 | 25 | 459.80 | 1213.90 | 603.65 | 2761.75 | 50 | 389.80 | 1137.54 | 521.51 | 2761.75 |
| | V2 | 25 | 235.77 | 732.83 | 326.38 | 1373.28 | 25 | 294.24 | 748.33 | 453.19 | 2254.18 | 50 | 235.77 | 740.58 | 390.94 | 2254.18 |
| | V3 | 24 | 3.16 | 492.37 | 295.41 | 1083.60 | 25 | 247.56 | 514.36 | 301.40 | 1523.92 | 49 | 3.16 | 503.59 | 295.57 | 1523.92 |

FIG. 6

INFANT FORMULA SYSTEM WITH ADAPTIVE LEVELS OF HUMAN MILK OLIGOSACCHARIDES (HMOS)

CROSS REFERENCE TO RELATED APPLICATIONS

The present application is a National Stage of International Application No. PCT/EP2015/071930, filed on Sep. 24, 2015, which claims priority to European Patent Application No. 14186352.2, filed on Sep. 25, 2014, and European Patent Application No. 15159584.0, filed on Mar. 18, 2015, the entire contents of which are being incorporated herein by reference.

FIELD OF THE INVENTION

The present invention relates to an age-tailored nutritional composition system comprising human milk oligosaccharides (HMOs), wherein the amount of HMOs present in each nutritional composition is selected according to the age of the infants. The invention further relates to the use of said age-tailored nutritional composition system for providing a health benefit to infants.

The invention also relates to an infant nutrition kit comprising a set of age-tailored nutritional compositions and to an infant nutrition regimen comprising feeding said age-tailored nutritional compositions.

Finally, the invention relates to a method for manufacturing a set of age-tailored nutritional compositions for infants.

BACKGROUND OF THE INVENTION

Breast milk is the most nutritionally sound food for babies. It consists of nutrients, such as proteins, lipids, carbohydrates, minerals, vitamins, and trace elements that babies need to grow healthy. It also contains immune-related components such as IgA, leukocytes, oligosaccharides, lysozyme, lactoferrin, interferon-γ, nucleotides, cytokines, and others. Several of these compounds offer passive protection in the gastrointestinal tract and to some extent in the upper respiratory tract, preventing adherence of pathogens to the mucosa and thereby protecting the breast-fed infant against invasive infections. Human milk also contains essential fatty acids, enzymes, hormones, growth factors, polyamines, and other biologically active compounds, which may play an important role in the health benefits associated with breast-feeding.

In cases where women are unable to feed their child with their own milk or cannot supply enough milk, or when breastfeeding is contraindicated, babies may be fed infant formulae.

Infant formulae are designed for babies and infants under 12 months of age. They aim at simulating human milk or its suitability as a complete or partial substitute for human milk.

Recently, human milk oligosaccharides (HMOs) have been included into infant formulae. For example, WO2012156273 discloses a method for the manufacture of an infant formula or an infant nutritional product comprising mixture of human milk oligosaccharides. Based on dry mass, HMOs are the third largest milk compound group present in human milk. They play a vital role in the early development of young children. Over 130 individual structures have been identified to date but the functional implications of this diversity are not yet known. The majority of the oligosaccharides in milk are not digestible by human infants. Thus, HMOs may serve as prebiotics in the form of indigestible carbohydrates that are selectively fermented by desirable gut microbiota. Furthermore, the known effects of HMOs in the maturation of the immune system and their prognostic use as immunomodulators underline their importance for the healthy development of infants in their first year of life.

For many HMOs a very large concentration range has been reported in the prior art.

This variation might be in part due to inappropriate sampling procedures during a feed, nutritional habits and Lewis and secretor status of the mother. Such variables are generally insufficiently described in the prior art regarding HMOs in breast milk. Furthermore, analytical methods used in the prior art are not always state of the art and validated for HMOs quantification.

Recently, it was found that the level of some particular HMOs evolves in human breast milk during the lactation period. For example, Chaturvedi et al. hypothesize that changes in milk oligosaccharide patterns are an intrinsic characteristic of human lactation after 26 weeks and that this period may be a period of dramatic changes in fucosylologosaccharide concentrations (Chaturvedi et al., 2001; *Fucosylated human milk oligosaccharides vary between individuals and over course of lactation*, Glycobiology vol. 11, no. 5, pp. 365-372).

This suggests that the need of HMOs in an infant evolves over the time from infant's birth to the end of the lactation period, and thus cannot be matched by a unique HMO load.

OBJECT OF THE INVENTION

There is still a need for providing infants with nutritional solutions that reflect the evolving nutritional needs of the infants over time and, in particular, better mimic the evolving nutritional quality and composition of breast milk during the lactation period. More specifically, there is still a need for compositions that are adapted in terms of their HMOs content, wherein said compositions particularly address the needs of infants of a given age.

Therefore, it was an object of the present invention to provide an improved infant nutrition system which takes into account the evolving nutritional needs of infants. More specifically, the invention aimed at developing a nutritional composition system for infants providing HMOs in ranges matching closely the mother's milk physiological levels in at least the first 2 months of life of the infants, and thereby delivering the same functionalities.

These objects are solved by means of the independent claims. The dependent claims further develop the central idea of the invention.

SUMMARY OF THE INVENTION

In a first aspect, the invention relates to an age-tailored nutritional composition system comprising at least one nutritional composition A for infants from 0 up to 1 month of age and at least one nutritional composition B for infants above 1 month and up to 2 months of age, wherein the nutritional compositions A and B comprise human milk oligosaccharides (HMOs), and wherein said nutritional compositions A and B differ from each other in the amount of HMOs present therein.

In a preferred embodiment of this first aspect, the age-tailored nutritional composition system further comprises at least one nutritional composition C for infants above 2 months and up to 4 months of age, preferably wherein the nutritional compositions C comprise human milk oligosaccharides (HMOs), and more preferably wherein nutritional compositions A, B and C differ from each other in the amount of HMOs present therein.

In another preferred embodiment, the invention relates to the age-tailored nutritional composition system according to the first aspect, wherein the amounts of HMOs present in each nutritional composition are selected according to the age of the infants.

In yet another preferred embodiment of the first aspect of the invention, the HMOs are present in a nutritional composition in a total amount of from 500 to 10000 mg/L, preferably from 1000 to 8000 mg/L, from 1500 to 5000 mg/L or from 1800 to 4000 mg/L of composition. HMOs may also be present in a nutritional composition in a total amount of from 1863 to 3673 mg/L, from 1883 to 3632 mg/L, from 1902 to 3590 mg/L, from 2000 to 3500 mg/L, from 2500 to 3000 mg/L, from 2558 to 2602 mg/L or in an amount of 2580 mg/L of composition. There may be one or several HMOs in the different nutritional compositions.

In yet another preferred embodiment of the age-tailored nutritional composition system according to the first aspect, the amount of HMOs present in the at least one nutritional composition A exceeds the amount of HMOs present in the at least one nutritional composition B, and the amount of HMOs present in the at least one nutritional composition B exceeds the amount of HMOs present in the at least one nutritional composition C.

In a particular embodiment, the age-tailored nutritional composition system of the invention may further comprise at least one nutritional composition D for infants above 4 months of age, and, optionally, any further nutritional compositions E, F, G, H, I, etc. Also this at least one nutritional composition D and the optional further nutritional compositions (E, F, etc.), may comprise HMOs, wherein the at least one composition D and the optional further nutritional compositions (E, F, etc.) preferably differ from nutritional compositions A, B and C in the amount of HMOs present therein. More preferably, the amount of HMOs present in each of these nutritional compositions A, B and C exceeds the amount of HMOs present in the at least one nutritional composition D and, optionally, any further nutritional compositions (E, F, etc.). It is particularly preferred that the amount of HMOs present in the at least one nutritional composition D exceeds the amount of HMOs present in the at least one nutritional composition E, the amount of HMOs present in the at least one nutritional composition E exceeds the amount of HMOs present in the at least one nutritional composition F, etc.

In a yet further preferred embodiment of the age-tailored nutritional composition system according to the first aspect, the at least one nutritional composition A comprises HMOs in a total amount of from 1000 to 10000 mg/L, preferably from 1500 to 8000 mg/L, more preferably from 2000 to 5000 mg/L, even more preferably from 3000 to 4000 mg/L, even more preferably from 3590 to 3673 mg/L, and most preferably in an amount of 3632 mg/L of composition.

In a yet further preferred embodiment of the age-tailored nutritional composition system according to the first aspect, the at least one nutritional composition B comprises HMOs in an amount of from 1500 to 3500 mg/L, preferably from 2000 to 3000 mg/L, more preferably from 2558 to 2602 mg/L, and most preferably in an amount of 2580 mg/L of composition.

In a yet further preferred embodiment of the age-tailored nutritional composition system according to the first aspect, the at least one nutritional composition C comprises HMOs in an amount of from 500 to 2500 mg/L, preferably from 1500 to 2000 mg/L, more preferably from 1863 to 1902 mg/L, and most preferably in an amount of 1883 mg/L of composition.

In a particular embodiment, the age-tailored nutritional composition system according to the first aspect comprises two nutritional compositions A for infants from 0 up to 1 month of age. Preferably, the two nutritional compositions A are a first nutritional composition A1 for infants from 0 up to 3-7 days of age and a second nutritional composition A2 for the rest of the time period up to 1 month of age. For instance, the two nutritional compositions A may be a first nutritional composition A1 for infants from 0 up to 7 days of age and a second nutritional composition A2 for infants from 8 days up to 1 month of age. The two nutritional compositions A may also be a first nutritional composition A1 for infants from 0 up to 6 days of age and a second nutritional composition A2 for infants from 7 days up to 1 month of age, or a first nutritional composition A1 for infants from 0 up to 5 days of age and a second nutritional composition A2 for infants from 6 days up to 1 month of age, or a first nutritional composition A1 for infants from 0 up to 4 days of age and a second nutritional composition A2 for infants from 5 days up to 1 month of age, or a first nutritional composition A1 for infants from 0 up to 3 days of age and a second nutritional composition A2 for infants from 4 days up to 1 month of age. These nutritional compositions A1 and A2 preferably comprise human milk oligosaccharides (HMOs), wherein, preferably, the amounts of HMOs present in each nutritional composition A1 and A2 are selected according to the age of the infants. More preferably, nutritional compositions A1 and A2 differ from each other in the amount of HMOs present therein. It is particularly preferred that the amount of HMOs present in nutritional composition A1 exceeds the amount of HMOs present in nutritional composition A2. Said first nutritional composition A1 may preferably comprise HMOs in an amount of from 5000 to 10000 mg/L, and more preferably from 5000 to 8000 mg/L of composition. The second nutritional composition A2 may preferably comprise HMOs in an amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition.

In another particular embodiment, the age-tailored nutritional composition system according to the first aspect comprises three nutritional compositions A for infants from 0 up to 1 month of age. Preferably, the three nutritional compositions A are a first nutritional composition A1 for infants from 0 up to 5 days, a second nutritional composition A2 for infants from 6 up to 15 days and a third nutritional composition A3 for infants for the rest of the time period up to 1 month of age (i.e. from 16 days up to 30 or 31 days). These nutritional compositions A1, A2 and A3 preferably comprise human milk oligosaccharides (HMOs), wherein, preferably, the amounts of HMOs present in each nutritional composition A1, A2 and A3 are selected according to the age of the infants. More preferably, nutritional compositions A1, A2 and A3 differ from each other in the amount of HMOs present therein. It is particularly preferred that the amount of HMOs present in nutritional composition A1 exceeds the amount of HMOs present in nutritional composition A2, and that the amount of HMOs present in nutritional composition A2 exceeds the amount of HMOs present in nutritional composition A3. Said first nutritional composition A1 may preferably comprise HMOs in an amount of from 5000 to 10000 mg/L, and more preferably from 5000 to 8000 mg/L of composition. The second nutritional composition A2 may preferably comprise HMOs in an amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition. The third nutritional composition A3 may preferably comprise HMOs in an amount of from 500 to 4500 mg/L, preferably from 1000 to 4000 mg/L, more preferably from 2000 to 3500 mg/L, more preferably from 3000 to 3500 mg/L of the composition.

In another preferred embodiment, the invention relates to the age-tailored nutritional composition system according to the first aspect, wherein the HMOs are selected from HMOs which are naturally present in human breast milk.

In yet another preferred embodiment of the age-tailored nutritional composition system according to the first aspect, the HMOs are selected from "sialylated oligosaccharides", "fucosylated oligosaccharides", "N-acetylated oligosaccharides" or any mixtures thereof.

In yet another preferred embodiment of the age-tailored nutritional composition system according to the first aspect, the HMOs are selected from 2'Fucosyllactose (2'FL or 2FL or 2-FL), 3'Sialyllactose (3'SL or 3SL or 3-SL), 6'Sialyllactose (6'SL or 6SL or 6-SL), Lacto-N-neotetraose (LNnT), Lacto-N-tetraose (LNT), or any combination thereof.

It is particularly preferred that each one of 2'Fucosyllactose (2'FL, 2FL or 2-FL), 3'Sialyllactose (3'SL, 3SL, or 3-SL), 6'Sialyllactose (6'SL, 6SL or 6-SL), Lacto-N-neotetraose (LNnT) and Lacto-N-tetraose (LNT) is present in a nutritional composition of the age-tailored nutritional composition system of the first aspect in an amount of from 50 to 5000 mg/L of composition, or in an amount of from 70 to 4000 mg/L, from 80 to 3000 mg/L, from 95 to 2000 mg/L, from 100 to 1700 mg/L, from 125 to 1400 mg/L, from 130 to 1300 mg/L, from 150 to 920 mg/L, from 190 to 900 mg/L, from 200 to 800 mg/L, from 205 to 650 mg/L, from 231 to 600 mg/L, from 239 to 550 mg/L, from 240 to 540 mg/L, from 250 to 500 mg/L, from 255 to 400 mg/L, from 280 to 350 mg/L, or 300 mg/L of composition.

In a further preferred embodiment of the age-tailored nutritional composition system according to the first aspect, 2'Fucosyllactose is present in a nutritional composition in an amount of from 500 to 5000 mg/L, preferably from 800 to 4000 mg/L, from 900 to 2000 mg/L, from 920 to 1700 mg/L, from 949 to 1520 mg/L, from 980 to 1500 mg/L, from 1000 to 1484 mg/L, from 1000 to 1450 mg/L, from 1200 to 1300 mg/L, or from 1206 to 1210 mg/L of composition.

In a further preferred embodiment of the age-tailored nutritional composition system according to the first aspect, 3'Sialyllactose is present in a nutritional composition in an amount of from 150 to 280 mg/L, preferably from 190 to 250 mg/L, from 200 to 240 mg/L, from 205 to 231 mg/L, from 210 to 230 mg/L, from 211 to 225 mg/L, or from 215 to 220 mg/L of composition.

In a further preferred embodiment of the age-tailored nutritional composition system according to the first aspect, 6'Sialyllactose is present in a nutritional composition in an amount of from 80 to 650 mg/L, preferably from 100 to 600 mg/L, from 125 to 550 mg/L, from 130 to 540 mg/L, from 135 to 530 mg/L, from 150 to 500 mg/L, from 180 to 450 mg/L, from 200 to 350 mg/L, from 250 to 300 mg/L, from 270 to 280 mg/L, or from 272 to 275 mg/L of composition.

In a further preferred embodiment of the age-tailored nutritional composition system according to the first aspect, Lacto-N-neotetraose is present in a nutritional composition in an amount of from 50 to 350 mg/L, preferably from 70 to 280 mg/L, from 80 to 255 mg/L, from 95 to 239 mg/L, from 100 to 220 mg/L, from 110 to 200 mg/L, from 120 to 180 mg/L, from 130 to 165 mg/L, or from 148 to 150 mg/L composition.

In a further preferred embodiment of the age-tailored nutritional composition system according to the first aspect, Lacto-N-tetraose is present in a nutritional composition in an amount of from 200 to 4000 mg/L, preferably from 250 to 3000 mg/L, from 300 to 1400 mg/L, from 400 to 1300 mg/L, from 490 to 1215 mg/L, from 500 to 1138 mg/L, from 504 to 1060 mg/L, from 515 to 1000 mg/L, from 600 to 850 mg/L, from 700 to 800 mg/L, from 730 to 750 mg/L, or from 735 to 741 mg/L of composition.

In another preferred embodiment of the age-tailored nutritional composition system according to the first aspect, 2'Fucosyllactose is present in the at least one nutritional composition A in an amount of from 500 to 5000 mg/L, preferably from 900 to 4000 mg/L, more preferably from 1000 to 2000 mg/L, even more preferably from 1300 to 1700 mg/L, even more preferably from 1450 to 1520 mg/L, most preferably 1484 mg/L of composition.

In another preferred embodiment of the age-tailored nutritional composition system according to the first aspect, 2'Fucosyllactose is present in the at least one nutritional composition B in an amount of from 1000 to 1500 mg/L, preferably from 1100 to 1300 mg/L, more preferably from 1200 to 1210 mg/L, most preferably 1206 mg/L of composition.

In another preferred embodiment of the age-tailored nutritional composition system according to the first aspect, 2'Fucosyllactose is present in the at least one nutritional composition C in an amount of from 800 to 1200 mg/L, preferably from 900 to 1000 mg/L, more preferably from 920 to 980 mg/L, most preferably 949 mg/L of composition.

In another preferred embodiment of the age-tailored nutritional composition system according to the first aspect, 3'Sialyllactose is present in the at least one nutritional composition A in an amount of from 200 to 280 mg/L, preferably from 210 to 250 mg/L, more preferably from 225 to 240 mg/L, most preferably 231 mg/L of composition.

In another preferred embodiment of the age-tailored nutritional composition system according to the first aspect, 3'Sialyllactose is present in the at least one nutritional composition B in an amount of from 150 to 250 mg/L, preferably from 190 to 230 mg/L, more preferably from 200 to 225 mg/L, most preferably 211 mg/L of composition.

In another preferred embodiment of the age-tailored nutritional composition system according to the first aspect, 3'Sialyllactose is present in the at least one nutritional composition C in an amount of from 150 to 250 mg/L preferably from 180 to 220 mg/L, more preferably from 200 to 210 mg/L, most preferably 205 mg/L of composition.

In another preferred embodiment of the age-tailored nutritional composition system according to the first aspect, 6'Sialyllactose is present in the at least one nutritional composition A in an amount of from 450 to 650 mg/L, preferably from 500 to 600 mg/L, more preferably from 530 to 550 mg/L, most preferably 540 mg/L of composition.

In another preferred embodiment of the age-tailored nutritional composition system according to the first aspect, 6'Sialyllactose is present in the at least one nutritional composition B in an amount of from 200 to 350 mg/L, preferably from 250 to 300 mg/L, more preferably from 270 to 280 mg/L, most preferably 275 mg/L of composition.

In another preferred embodiment of the age-tailored nutritional composition system according to the first aspect, 6'Sialyllactose is present in the at least one nutritional composition C in an amount of from 80 to 180 mg/L, preferably from 100 to 150 mg/L, more preferably from 125 to 135 mg/L, most preferably 130 mg/L of composition.

In another preferred embodiment of the age-tailored nutritional composition system according to the first aspect, Lacto-N-neotetraose is present in the at least one nutritional composition A in an amount of from 150 to 350 mg/L, preferably from 200 to 280 mg/L, more preferably from 220 to 255 mg/L, most preferably 239 mg/L of composition.

In another preferred embodiment of the age-tailored nutritional composition system according to the first aspect, Lacto-N-neotetraose is present in the at least one nutritional composition B in an amount of from 100 to 200 mg/L, preferably from 120 to 180 mg/L, more preferably from 130 to 165 mg/L, most preferably 148 mg/L of composition.

In another preferred embodiment of the age-tailored nutritional composition system according to the first aspect, Lacto-N-neotetraose is present in the at least one nutritional composition C in an amount of from 50 to 150 mg/L, preferably from 70 to 120 mg/L, more preferably from 80 to 110 mg/L, most preferably 95 mg/L of composition.

In another preferred embodiment of the age-tailored nutritional composition system according to the first aspect, Lacto-N-tetraose is present in the at least one nutritional composition A in an amount of from 600 to 4000 mg/L, preferably from 700 to 3000 mg/L, more preferably from 800 to 1400 mg/L, even more preferably from 1000 to 1300 mg/L, even more preferably from 1060 to 1215 mg/L, most preferably 1138 mg/L of composition.

In another preferred embodiment of the age-tailored nutritional composition system according to the first aspect, Lacto-N-tetraose is present in the at least one nutritional composition B in an amount of from 500 to 1000 mg/L, preferably from 600 to 850 mg/L, more preferably from 730 to 750 mg/L, most preferably 741 mg/L of composition.

In another preferred embodiment of the age-tailored nutritional composition system according to the first aspect, Lacto-N-tetraose is present in the at least one nutritional composition C in an amount of from 300 to 700 mg/L, preferably from 400 to 600 mg/L, more preferably from 490 to 515 mg/L, most preferably 504 mg/L of composition.

In a second aspect, the invention relates to the age-tailored nutritional composition system according to the first aspect for use in providing a suitable nutrition to infants.

In a third aspect the invention relates to the use of the age-tailored nutritional composition system according to the first aspect for feeding an infant.

In a fourth aspect the invention relates to the age-tailored nutritional composition system according to the first aspect for use in providing a health benefit to infants, wherein the health benefit is preferably selected from treatment or prevention of diarrhea, treatment or prevention of gut discomfort, weaning facilitation, maturation of the immune system, prevention or management of allergy, reducing cardiovascular diseases later in life, reducing risk of obesity, reducing risk of infections, ensuring a normal growth curve, improving or insuring optimal cognition, improved immune function and immune defenses, prevention of upper respiratory tract infections like otitis media or common cold.

In a fifth aspect, the invention relates to an infant nutrition kit comprising a set of age-tailored nutritional compositions according to the first aspect.

In a preferred embodiment of the infant nutrition kit of the third aspect, the nutritional compositions are packed in single dose units, preferably wherein each single dose unit comprises a sufficient amount of nutritional composition to prepare a single serving upon reconstitution with water, more preferably wherein the single dose unit is a capsule.

In a sixth aspect, the invention relates to a method for the manufacture of a set of nutritional compositions for infants comprising the steps of preparing at least one nutritional composition A for infants from 0 up to 1 month of age and at least one nutritional composition B for infants above 1 month and up to 2 months of age, wherein preparation of each composition comprises blending together at least a protein source, a carbohydrate source, and a fat source; selecting for each of the at least one nutritional composition A and the at least one nutritional composition B an amount of HMOs according to the age of the infants, and incorporating said selected amount of HMOs into the corresponding nutritional composition, such that said nutritional compositions A and B differ from each other in the amount of HMOs present therein.

In a preferred embodiment, the method according to the sixth aspect further comprises the steps of preparing at least one nutritional composition C for infants above 2 months and up to 4 months of age, selecting for said nutritional composition C an amount of HMOs according to the age of the infants, and incorporating said selected amount of HMOs into at least one nutritional composition C, preferably such that the nutritional compositions A and B and C differ from each other in the amount of HMOs present therein.

In a preferred embodiment of the method according to the sixth aspect the HMOs are selected for a nutritional composition in a total amount of from 500 to 10000 mg/L, preferably from 1000 to 8000 mg/L, from 1500 to 5000 mg/L or from 1800 to 4000 mg/L of composition. Preferably the HMOs are selected for a nutritional composition in a total amount of from 1863 to 3673 mg/L, from 1883 to 3632 mg/L, from 1902 to 3590 mg/L, from 2000 to 3500 mg/L, from 2500 to 3000 mg/L, from 2558 to 2602 mg/L or in an amount of 2580 mg/L of composition.

In yet another preferred embodiment of the method according to the sixth aspect, the amount of HMOs selected for the at least one nutritional composition A exceeds the amount of HMOs selected for the at least one nutritional composition B, and the amount of HMOs selected for the at least one nutritional composition B exceeds the amount of HMOs selected for the at least one nutritional composition C.

In another embodiment, the method according to the sixth aspect further comprises the step of preparing at least one nutritional composition D for infants above 4 months of age and, optionally, any further nutritional compositions E, F, G, H, I, etc., selecting for said at least one nutritional composition D and, optionally, for each of said further nutritional compositions (E, F, etc.) an amount of HMOs according to the age of the infants, and incorporating said selected amount of HMOs into the at least one nutritional composition D and, optionally, into the further nutritional compositions (E, F, etc.), respectively. Preferably, an amount of HMOs is selected for the at least one nutritional composition D and, optionally, for each of said further nutritional compositions (E, F, etc.), such that the nutritional compositions A, B, C, D and, optionally, any further nutritional compositions E, F, etc. differ from each other in the amount of HMOs present therein. More preferably, the amount of HMOs selected for each one of nutritional compositions A, B and C exceeds the amount of HMOs selected for the at least one nutritional composition D and, optionally, for any further nutritional compositions E, F, etc. It is particularly preferred that the amount of HMOs selected for the at least one nutritional composition D exceeds the amount of HMOs selected for the at least one nutritional composition E, the amount of HMOs selected for the at least one nutritional composition E exceeds the amount of HMOs selected for the at least one nutritional composition F, etc.

In a yet further preferred embodiment of the method according to the sixth aspect, HMOs are selected for the at least one nutritional composition A in a total amount of from 1000 to 10000 mg/L, preferably from 1500 to 8000 mg/L, more preferably from 2000 to 5000 mg/L, even more preferably from 3000 to 4000 mg/L, even more preferably from 3590 to 3673 mg/L, and most preferably in an amount of 3632 mg/L of composition.

In a yet further preferred embodiment of the method according to the sixth aspect HMOs are selected for the at least one nutritional composition B in an amount of from 1500 to 3500 mg/L, preferably from 2000 to 3000 mg/L, more preferably from 2558 to 2602 mg/L, and most preferably in an amount of 2580 mg/L of composition.

In a yet further preferred embodiment of the method according to the sixth aspect, HMOs are selected for the at least one nutritional composition C in an amount of from 500 to 2500 mg/L, preferably from 1500 to 2000 mg/L, more preferably from 1863 to 1902 mg/L, and most preferably in an amount of 1883 mg/L of composition.

In another preferred embodiment of the method according to the sixth aspect, the step of preparing at least one nutritional composition A for infants from 0 up to 1 month of age comprises preparing two nutritional compositions A. Preferably, these two nutritional compositions A are a first nutritional composition A1 for infants from 0 up to 3-7 days of age and a second nutritional composition A2 for the rest of the time period up to 1 month of age. For instance, the two nutritional compositions A may be a first nutritional composition A1 for infants from 0 up to 7 days of age, and a second nutritional composition A2 for infants from 8 days up to 1 month of age, or a first nutritional composition A1 for infants from 0 up to 6 days of age and a second nutritional composition A2 for infants from 7 days up to 1 month of age, or a first nutritional composition A1 for infants from 0 up to 5 days of age and a second nutritional composition A2 for infants from 6 days up to 1 month of age, or a first nutritional composition A1 for infants from 0 up to 4 days of age and a second nutritional composition A2 for infants from 5 days up to 1 month of age, or a first nutritional composition A1 for infants from 0 up to 3 days of age and a second nutritional composition A2 for infants from 4 days up to 1 month of age.

It is preferred that for each of nutritional compositions A1 and A2 an amount of HMOs is selected according to the age of the infants, more preferably wherein said amount of HMOs is selected such that nutritional compositions A1 and A2 differ from each other in the amount of HMOs present therein. It is particularly preferred that for each of nutritional compositions A1 and A2 the amount of HMOs is selected such that the amount of HMOs selected for nutritional composition A1 exceeds the amount of HMOs selected for nutritional composition A2.

For nutritional composition A1 the HMOs may be selected in an amount of from 5000 to 10000 mg/L, and preferably from 5000 to 8000 mg/L of composition. For nutritional composition A2 the HMOs be selected in an amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition.

In another particular embodiment of the method according to the sixth aspect, the step of preparing at least one nutritional composition A for infants from 0 up to 1 month of age comprises preparing three nutritional compositions A. Preferably, these three nutritional compositions A are a first nutritional composition A1 for infants from 0 up to 5 days, a second nutritional composition A2 for infants from 6 up to 15 days and a third nutritional composition A3 for infants for the rest of the time period up to 1 month of age (i.e. from 16 days up to 30 or 31 days). These nutritional compositions A1, A2 and A3 preferably comprise human milk oligosaccharides (HMOs), wherein, preferably, the amounts of HMOs present in each nutritional composition A1, A2 and A3 are selected according to the age of the infants. More preferably, nutritional compositions A1, A2 and A3 differ from each other in the amount of HMOs present therein. It is particularly preferred that the amount of HMOs present in nutritional composition A1 exceeds the amount of HMOs present in nutritional composition A2, and that the amount of HMOs present in nutritional composition A2 exceeds the amount of HMOs present in nutritional composition A3. Said first nutritional composition A1 may preferably comprise HMOs in an amount of from 5000 to 10000 mg/L, and more preferably from 5000 to 8000 mg/L of composition. The second nutritional composition A2 may preferably comprise HMOs in an amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition. The third nutritional composition A3 may preferably comprise HMOs in an amount of from 500 to 4500 mg/L, preferably from 1000 to 4000 mg/L, more preferably from 2000 to 3500 mg/L, more preferably from 3000 to 3500 mg/L of the composition.

In another preferred embodiment of the method according to the sixth aspect, the selected amount of HMOs is incorporated into the corresponding nutritional composition during preparation of said composition, preferably by blending the HMOs together with the protein source, the carbohydrate source, and the fat source.

In yet another preferred embodiment of the method according to the sixth aspect, the selected amount of HMOs is incorporated into the corresponding nutritional composition by preparing said composition in a first step and adding the HMOs to the ready prepared composition in a second step.

In another preferred embodiment, the invention relates to the method according to the sixth aspect, wherein the HMOs are selected from HMOs which are naturally present in human breast milk.

It is particularly preferred that the HMOs are selected from "sialylated oligosaccharides", "fucosylated oligosaccharides", "N-acetylated oligosaccharides" or any mixtures thereof. Even more preferably, the HMOs are selected from 2'Fucosyllactose (2'FL, 2FL, or 2-FL), 3'Sialyllactose (3'SL, 3SL or 3-SL), 6'Sialyllactose (6'SL, 6SL or 6-SL), Lacto-N-neotetraose (LNnT), Lacto-N-tetraose (LNT), or any combination thereof.

It is also particularly preferred that each one of 2'Fucosyllactose (2'FL, 2FL or 2-FL), 3'Sialyllactose (3'SL, 3SL, or 3-SL), 6'Sialyllactose (6'SL, 6SL or 6-SL), Lacto-N-neotetraose (LNnT) and Lacto-N-tetraose (LNT) is selected for a nutritional composition of the age-tailored nutritional composition system of the sixth aspect in an amount of from 50 to 5000 mg/L of composition, and more preferably in an amount of from 70 to 4000 mg/L, from 80 to 3000 mg/L, from 95 to 2000 mg/L, from 100 to 1700 mg/L, from 125 to 1400 mg/L, from 130 to 1300 mg/L, from 150 to 920 mg/L, from 190 to 900 mg/L, from 200 to 800 mg/L, from 205 to 650 mg/L, from 231 to 600 mg/L, from 239 to 550 mg/L, from 240 to 540 mg/L, from 250 to 500 mg/L, from 255 to 400 mg/L, from 280 to 350 mg/L, or 300 mg/L of composition.

In a further preferred embodiment of the method according to the sixth aspect, 2'Fucosyllactose is selected for a nutritional composition in an amount of from 500 to 5000 mg/L, preferably from 800 to 4000 mg/L, from 900 to 2000 mg/L, from 920 to 1700 mg/L, from 949 to 1520 mg/L, from 980 to 1500 mg/L, from 1000 to 1484 mg/L, from 1000 to 1450 mg/L, from 1200 to 1300 mg/L, or from 1206 to 1210 mg/L of composition.

In a further preferred embodiment of the method according to the sixth aspect, 3'Sialyllactose is selected for a nutritional composition in an amount of from 150 to 280 mg/L, preferably from 190 to 250 mg/L, from 200 to 240 mg/L, from 205 to 231 mg/L, from 210 to 230 mg/L, from 211 to 225 mg/L, or from 215 to 220 mg/L of composition.

In a further preferred embodiment of the method according to the sixth aspect, 6'Sialyllactose is selected for a nutritional composition in an amount of from 80 to 650 mg/L, preferably from 100 to 600 mg/L, from 125 to 550 mg/L, from 130 to 540 mg/L, from 135 to 530 mg/L, from 150 to 500 mg/L, from 180 to 450 mg/L, from 200 to 350 mg/L, from 250 to 300 mg/L, from 270 to 280 mg/L, or from 272 to 275 mg/L of composition.

In a further preferred embodiment of the method according to the sixth aspect, Lacto-N-neotetraose is selected for a nutritional composition in an amount of from 50 to 350 mg/L, preferably from 70 to 280 mg/L, from 80 to 255 mg/L, from 95 to 239 mg/L, from 100 to 220 mg/L, from 110 to 200 mg/L, from 120 to 180 mg/L, from 130 to 165 mg/L, or from 148 to 150 mg/L composition.

In a further preferred embodiment of the method according to the sixth aspect, Lacto-N-tetraose is selected for a nutritional composition in an amount of from 200 to 4000 mg/L, more preferably from 250 to 3000 mg/L, from 300 to 1400 mg/L, from 400 to 1300 mg/L, from 490 to 1215 mg/L, from 500 to 1138 mg/L, from 504 to 1060 mg/L, from 515 to 1000 mg/L, from 600 to 850 mg/L, from 700 to 800 mg/L, from 730 to 750 mg/L, or from 735 to 741 mg/L of composition.

In another preferred embodiment of the method according to the sixth aspect, 2'Fucosyllactose is selected for the at least one nutritional composition A in an amount of from 500 to 5000 mg/L, preferably from 900 to 4000 mg/L, more preferably from 1000 to 2000 mg/L, even more preferably from 1300 to 1700 mg/L, even more preferably from 1450 to 1520 mg/L, most preferably 1484 mg/L of composition.

In another preferred embodiment of the method according to the sixth aspect, 2'Fucosyllactose is selected for the at least one nutritional composition B in an amount of from 1000 to 1500 mg/L, preferably from 1100 to 1300 mg/L, more preferably from 1200 to 1210 mg/L, most preferably 1206 mg/L of composition.

In another preferred embodiment of the method according to the sixth aspect, 2'Fucosyllactose is selected for the at least one nutritional composition C in an amount of from 800 to 1200 mg/L, preferably from 900 to 1000 mg/L, more preferably from 920 to 980 mg/L, most preferably 949 mg/L of composition.

In another preferred embodiment of the method according to the sixth aspect, 3'Sialyllactose is selected for the at least one nutritional composition A in an amount of from 200 to 280 mg/L, preferably from 210 to 250 mg/L, more preferably from 225 to 240 mg/L, most preferably 231 mg/L of composition.

In another preferred embodiment of the method according to the sixth aspect, 3'Sialyllactose is selected for the at least one nutritional composition B in an amount of from 150 to 250 mg/L, preferably from 190 to 230 mg/L, more preferably from 200 to 225 mg/L, most preferably 211 mg/L of composition.

In another preferred embodiment of the method according to the sixth aspect, 3'Sialyllactose is selected for the at least one nutritional composition C in an amount of from 150 to 250 mg/L preferably from 180 to 220 mg/L, more preferably from 200 to 210 mg/L, most preferably 205 mg/L of composition.

In another preferred embodiment of the method according to the sixth aspect, 6'Sialyllactose is selected for the at least one nutritional composition A in an amount of from 450 to 650 mg/L, preferably from 500 to 600 mg/L, more preferably from 530 to 550 mg/L, most preferably 540 mg/L of composition.

In another preferred embodiment of the method according to the sixth aspect, 6'Sialyllactose is selected for the at least one nutritional composition B in an amount of from 200 to 350 mg/L, preferably from 250 to 300 mg/L, more preferably from 270 to 280 mg/L, most preferably 275 mg/L of composition.

In another preferred embodiment of the method according to the sixth aspect, 6'Sialyllactose is selected for the at least one nutritional composition C in an amount of from 80 to 180 mg/L, preferably from 100 to 150 mg/L, more preferably from 125 to 135 mg/L, most preferably 130 mg/L of composition.

In another preferred embodiment of the method according to the sixth aspect, Lacto-N-neotetraose is selected for the at least one nutritional composition A in an amount of from 150 to 350 mg/L, preferably from 200 to 280 mg/L, more preferably from 220 to 255 mg/L, most preferably 239 mg/L of composition.

In another preferred embodiment of the method according to the sixth aspect, Lacto-N-neotetraose is selected for the at least one nutritional composition B in an amount of from 100 to 200 mg/L, preferably from 120 to 180 mg/L, more preferably from 130 to 165 mg/L, most preferably 148 mg/L of composition.

In another preferred embodiment of the method according to the sixth aspect, Lacto-N-neotetraose is selected for the at least one nutritional composition C in an amount of from 50 to 150 mg/L, preferably from 70 to 120 mg/L, more preferably from 80 to 110 mg/L, most preferably 95 mg/L of composition.

In another preferred embodiment of the method according to the sixth aspect, Lacto-N-tetraose is selected for the at least one nutritional composition A in an amount of from 600 to 4000 mg/L, preferably from 700 to 3000 mg/L, more preferably from 800 to 1400 mg/L, even more preferably from 1000 to 1300 mg/L, even more preferably from 1060 to 1215 mg/L, most preferably 1138 mg/L of composition.

In another preferred embodiment of the method according to the sixth aspect, Lacto-N-tetraose is selected for the at least one nutritional composition B in an amount of from 500 to 1000 mg/L, preferably from 600 to 850 mg/L, more preferably from 730 to 750 mg/L, most preferably 741 mg/L of composition.

In another preferred embodiment of the method according to the sixth aspect, Lacto-N-tetraose is selected for the at least one nutritional composition C in an amount of from 300 to 700 mg/L, preferably from 400 to 600 mg/L, more preferably from 490 to 515 mg/L, most preferably 504 mg/L of composition.

In a seventh aspect, the invention relates to an infant nutrition regimen comprising feeding an infant from 0 up to 1 month of age at least one nutritional composition A, feeding said infant above 1 month and up to 2 months of age at least one nutritional composition B, wherein the nutritional compositions A and B comprise human milk oligosaccharides (HMOs) and wherein said nutritional compositions A and B differ from each other in the amount of HMOs present therein.

In a preferred embodiment, the infant nutrition regimen according to the seventh aspect further comprises feeding said infant above 2 months and up to 4 months of age at least one nutritional composition C, preferably wherein the at least one nutritional composition C comprises human milk oligosaccharides (HMOs), and more preferably wherein the nutritional compositions A, B and C differ from each other in the amount of HMOs present therein.

In another preferred embodiment, the infant nutrition regimen according to the seventh aspect further comprises feeding said infant above 4 months of age at least one nutritional composition D and, optionally, any further nutritional compositions E, F, G, H, I, etc. Also this at least one nutritional composition D and the optional further nutritional compositions (E, F, etc.) may comprise HMOs, wherein the at least one composition D and the optional further nutritional compositions (E, F, etc.) preferably differ from nutritional compositions A, B and C in the amount of HMOs present therein.

In yet another preferred embodiment, the infant nutrition regimen according to the seventh aspect comprises feeding an infant from 0 up to 1 month of age two nutritional compositions A. Preferably, said two nutritional compositions A may be a first nutritional composition A1 for infants from 0 up to 3-7 days of age and a second nutritional composition A2 for the rest of the time period up to 1 month of age. For instance, the two nutritional compositions A may be a first nutritional composition A1 for infants from 0 up to 7 days of age and a second nutritional composition A2 for infants from 8 days up to 1 month of age, or a first nutritional composition A1 for infants from 0 up to 6 days of age and a second nutritional composition A2 for infants from 7 days up to 1 month of age, or a first nutritional composition A1 for infants from 0 up to 5 days of age and a second nutritional composition A2 for infants from 6 days up to 1 month of age, or a first nutritional composition A1 for infants from 0 up to 4 days of age and a second nutritional composition A2 for infants from 5 days up to 1 month of age, or a first nutritional composition A1 for infants from 0 up to 3 days of age and a second nutritional composition A2 for infants from 4 days up to 1 month of age. These nutritional compositions A1 and A2 may comprise human milk oligosaccharides (HMOs), wherein, preferably, the amounts of HMOs present in each nutritional composition A1 and A2 are selected according to the age of the infants. More preferably, the nutritional compositions A1 and A2 differ from each other in the amount of HMOs present therein and most preferably the amount of HMOs present in nutritional composition A1 exceeds the amount of HMOs present in nutritional composition A2.

In another particular embodiment, the infant nutrition regimen according to the seventh aspect comprises feeding an infant from 0 up to 1 month of age three nutritional compositions A. Preferably, said three nutritional compositions A may be a first nutritional composition A1 for infants from 0 up to 5 days, a second nutritional composition A2 for infants from 6 up to 15 days and a third nutritional composition A3 for infants for the rest of the time period up to 1 month of age (i.e. from 16 days up to 30 or 31 days). These nutritional compositions A1, A2 and A3 preferably comprise human milk oligosaccharides (HMOs), wherein, preferably, the amounts of HMOs present in each nutritional composition A1, A2 and A3 are selected according to the age of the infants. More preferably, nutritional compositions A1, A2 and A3 differ from each other in the amount of HMOs present therein. It is particularly preferred that the amount of HMOs present in nutritional composition A1 exceeds the amount of HMOs present in nutritional composition A2, and that the amount of HMOs present in nutritional composition A2 exceeds the amount of HMOs present in nutritional composition A3. Said first nutritional composition A1 may preferably comprise HMOs in an amount of from 5000 to 10000 mg/L, and more preferably from 5000 to 8000 mg/L of composition. The second nutritional composition A2 may preferably comprise HMOs in an amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition. The third nutritional composition A3 may preferably comprise HMOs in an amount of from 500 to 4500 mg/L, preferably from 1000 to 4000 mg/L, more preferably from 2000 to 3500 mg/L, more preferably from 3000 to 3500 mg/L of the composition.

In a particularly preferred embodiment, the nutritional compositions A (e.g. A1, A2, A3), B, C, D, E, F, etc., of the infant nutrition regimen according to the seventh aspect correspond to the nutritional compositions A (e.g. A1, A2, A3), B, C, D, E, F, etc., according to the first aspect of the invention, respectively.

Other aspects and embodiments of the present invention are described below.

In an eighth aspect, the invention relates to a method for providing nutrition to an infant. This method may comprise:
feeding an infant from 0 up to 1 month of age at least one nutritional composition A,
feeding said infant above 1 month and up to 2 months of age at least one nutritional composition B;
wherein the nutritional compositions A and B comprise HMOs and wherein said nutritional compositions A and B differ from each other in the amount of HMOs present therein.

It may further comprise:
feeding said infant above 2 months and up to 4 months of age at least one nutritional composition C;
preferably wherein the at least one nutritional composition C comprises HMOs;
and more preferably wherein the nutritional compositions A, B and C differ from each other in the amount of HMOs present therein.

BRIEF DESCRIPTION OF THE FIGURES

FIG. 2 shows summary statistics of 2'Fucosyllactose concentrations in human breast milk at 1, 2 and 4 months post partum.

FIG. 3 shows summary statistics of 3'Sialyllactose concentrations in human breast milk at 1, 2 and 4 months post partum.

FIG. 4 shows summary statistics of Lacto-N-neotetraose concentrations in human breast milk at 1, 2 and 4 months post partum.

FIG. 5 shows summary statistics of 6'Sialyllactose concentrations in human breast milk at 1, 2 and 4 months post partum.

FIG. 6 shows summary statistics of Lacto-N-tetraose concentrations in human breast milk at 1, 2 and 4 months post partum.

DETAILED DESCRIPTION OF THE INVENTION

Figure 1A:
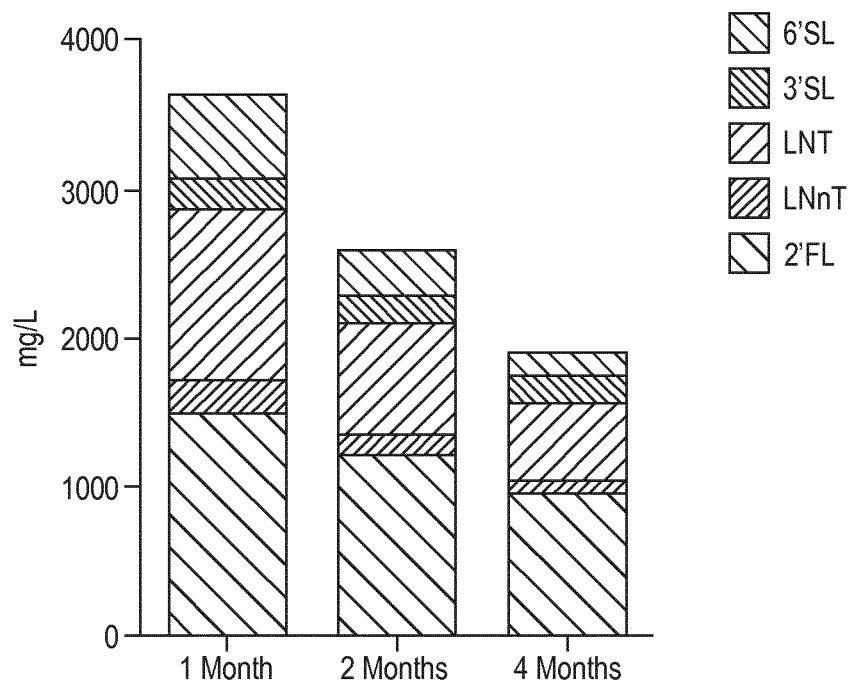
FIG. 1A depicts the evolving concentration of HMOs in mg/L of human milk over time.

The present invention provides an age-tailored nutritional composition system for infants.

In the context of the invention, the term "infants" means children under the age of 12 months.

The expressions "between 0 up to 1 month", "from 0 up to 1 month", "between birth up to 1 month", "from birth up to 1 month" can be used interchangeably.

Nutritional Compositions

As used herein, the expressions "composition(s)", "composition(s) of the invention", "nutritional composition(s)" and "nutritional composition(s) of the invention" are sought to refer to the nutritional compositions comprised in the age-tailored nutritional composition system of the invention.

In the present context, the term "nutritional composition" refers to any kind of composition that provides a nutritional benefit to an individual and that may be safely consumed by a human or animal. Said nutritional composition may be in solid, semi-solid or liquid form and may comprise one or more macronutrients, micronutrients, food additives, water, etc. For instance, the nutritional composition may comprise the following macronutrients: a source of proteins, a source of lipids, a source of carbohydrates and any combination thereof. Furthermore, the nutritional composition may comprise the following micronutrients: vitamins, minerals, fiber, phytochemicals, antioxidants, prebiotics, probiotics, and any combination thereof. The composition may also contain food additives such as stabilizers (when provided in solid form) or emulsifiers (when provided in liquid form).

The nutritional composition generally contains a protein source. The protein can be in an amount of from 1.6 to 3 g per 100 kcal, such as below 2.0 g per 100 kcal, e.g. from 1.8 to 2 g/100 kcal, or in an amount below 1.8 g per 100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed. In one particular embodiment the proteins of the composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition is a hypoallergenic nutritional composition.

The nutritional composition generally contains a carbohydrate source. This is particularly preferable in the case where the nutritional composition of the invention is an infant formula. In this case, any carbohydrate source conventionally found in infant formulae such as lactose, sucrose, maltodextrin, starch and mixtures thereof may be used although one of the preferred sources of carbohydrates is lactose.

The nutritional composition generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population. If necessary, the nutritional composition may contain emulsifiers and stabilisers such as soy, lecithin, citric acid esters of mono- and diglycerides, and the like.

The nutritional composition may contain probiotics. The term "probiotic" means microbial cell preparations or components of microbial cells with a beneficial effect on the health or well-being of the host. (Salminen S, Ouwehand A. Benno Y. et al. "Probiotics: how should they be defined" Trends Food Sci. Technol. 1999:10 107-10). The microbial cells are generally bacteria or yeasts.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp. In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition can further comprise at least one non-digestible oligosaccharide (e.g. prebiotics) other than the human milk oligosaccharides previously mentioned. Examples of prebiotics include certain oligosaccharides, such as fructooligosaccharides (FOS), galactooligosaccharides (GOS) and/or bovine's milk derived oligosaccharides (BMOs). They are usually in an amount between 0.3 and 10% by weight of composition. They may be in an amount between 2 and 8 g/l reconstituted nutritional composition (e.g. reconstituted formula).

The nutritional composition may be in the form of a nutritional product, preferably a food product, a nutritional supplement, a full meal, a nutritionally complete formula, a pharmaceutical formulation, functional food, a beverage product, and combinations thereof.

In a particular embodiment, the nutritional composition is a "synthetic nutritional composition" (i.e. not breast milk). The expression "synthetic composition" means a mixture obtained by chemical and/or biological means, which may be chemically identical to the mixture naturally occurring in mammalian milks.

Most preferably, the nutritional composition of the invention is in the form of a nutritional product which is adapted to the needs of an infant, such as an infant formula.

In the context of the invention, the expression "infant formula" means a nutritional product intended for particular nutritional use by infants during the first 12 months of life, which satisfies the nutritional requirements of said infants. It has to be understood that an infant formula can be either a complete or a partial substitute for human milk, i.e. that infants can be fed with the infant formula alone, or that the infant formula can be used as a complement of human milk. For further details on infant formulae it is referred to the Commission Directives 2006/141/EC of 22 Dec. 2006 and/or 91/321/EEC of 14 May 1991 on infant formulae and follow-on formulae, Article 1.2 (c). The expression "infant formula" encompasses both the "starter infant formula", i.e. a foodstuff intended for particular nutritional use by infants during the first four months of life and the "follow-on formula", i.e. a foodstuff intended for particular nutritional use by infants aged over four months and constituting the principal liquid element in the progressively diversified diet of this category of person.

Nutritional Composition System

As further used herein, the term "nutritional composition system" relates to a selection or range of at least two individual nutritional compositions according to the invention.

For instance, the nutritional composition system can be in the form of a nutritional product range or a range of nutritional products comprising at least two individual nutritional products, wherein each nutritional product of said range comprises an individual nutritional composition according to the invention.

Preferably, the nutritional composition system of the invention relates to a nutritional product range, wherein the nutritional products are infant formulae. These infant formulae may be formulated such that they provide either a complete or a partial substitute for human milk.

Human Milk Oligosaccharides (HMOs)

The term "HMO" or "HMOs" refers to human milk oligosaccharide(s). These carbohydrates are highly resistant to digestive enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

The HMOs comprised in the nutritional composition system of the invention are preferably "sialylated oligosaccharides", "fucosylated oligosaccharides", "N-acetylated oligosaccharides" or any mixtures thereof.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose). They may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

A "fucosylated oligosaccharide" is an oligosaccharide having a fucose residue. It has a neutral nature. Some examples are 2-FL (2' fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyl-lacto-N-neohexaose II and any combination thereof. In a preferred embodiment, it is 2-FL. The fucosylated oligosaccharide may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose) and LNnT (lacto-N-neotetraose). They may be synthesised chemically by enzymatic transfer of saccharide units from donor moieties to acceptor moieties using glycosyltransferases as described for example in U.S. Pat. No. 5,288,637 and WO 96/10086. Alternatively, they may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

The total amount of human milk oligosaccharides (HMOs) comprised in the nutritional compositions of the invention, preferably ranges from 500 to 10000 mg/L, more preferably from 1000 to 8000 mg/L, from 1500 to 5000 mg/L, from 1800 to 4000 mg/L, from 1863 to 3673 mg/L, from 1883 to 3632 mg/L, from 1902 to 3590 mg/L, from 2000 to 3500 mg/L, from 2500 to 3000 mg/L, or from 2558 to 2602 mg/L of composition.

Preferably, the HMOs comprised in the nutritional compositions of the invention are selected from HMOs which are naturally present in human breast milk. Examples of such HMOs include 2'Fucosyllactose (2'FL or 2FL or 2-FL), 3'Sialyllactose (3'SL or 3SL or 3-SL), 6'Sialyllactose (6'SL or 6SL or 6-SL), Lacto-N-neotetraose (LNnT), Lacto-N-tetraose (LNT).

2'Fucosyllactose may be present in a nutritional composition of the invention in an amount of from 500 to 5000 mg/L of composition. Preferably, 2'Fucosyllactose may be present in said nutritional composition in amount of from 800 to 4000 mg/L, from 900 to 2000 mg/L, from 920 to 1700 mg/L, from 949 to 1520 mg/L, from 980 to 1500 mg/L, from 1000 to 1484 mg/L, from 1000 to 1450 mg/L, from 1200 to 1300 mg/L, or from 1206 to 1210 mg/L of composition.

3'Sialyllactose may be present in a nutritional composition of the invention in an amount of from 150 to 280 mg/L of composition. Preferably, 3'Sialyllactose may be present in said nutritional composition in amount of from 190 to 250 mg/L, from 200 to 240 mg/L, from 205 to 231 mg/L, from 210 to 230 mg/L, from 211 to 225 mg/L, or from 215 to 220 mg/L of composition.

6'Sialyllactose may be present in a nutritional composition of the invention in an amount of from 80 to 650 mg/L of composition. Preferably, 6'Sialyllactose may be present in said nutritional composition in amount of from 100 to 600 mg/L, from 125 to 550 mg/L, from 130 to 540 mg/L, from 135 to 530 mg/L, from 150 to 500 mg/L, from 180 to 450 mg/L, from 200 to 350 mg/L, from 250 to 300 mg/L, from 270 to 280 mg/L, or from 272 to 275 mg/L of composition.

The 3'-Siallylactose (3'-SL) and 6'-Siallylactose (6'-SL) may be comprised in a nutritional composition in a weight ratio between 6:1 and 1:10, preferably between 5.9:1 and 1.5:10, such as between 5.86:1 and 1.53:10, for example in a ratio of 1:1. In a further particular embodiment, the 3'-Siallylactose (3'-SL) and 6'-Siallylactose (6'-SL) may be comprised in the nutritional compositions of the age-tailored nutritional composition system in a weight ratio that may evolve over time, for example in a similar way than the evolution of this ratio in the human breast milk. For example, the 3'SL:6'SL ratio may be 1.53:10 in the at least one nutritional composition A, then the 3'SL amount (and therefore also the 3'SL:6'SL ratio) may progressively increase in compositions B, C and in any other compositions (D, E, F . . . ).

Lacto-N-neotetraose may be present in a nutritional composition of the invention in an amount of from 50 to 350 mg/L of composition. Preferably, Lacto-N-neotetraose may be present in said nutritional composition in amount of from 70 to 280 mg/L, from 80 to 255 mg/L, from 95 to 239 mg/L, from 100 to 220 mg/L, from 110 to 200 mg/L, from 120 to 180 mg/L, from 130 to 165 mg/L, or from 148 to 150 mg/L of composition.

Lacto-N-tetraose may be present in a nutritional composition of the invention in an amount of from 200 to 4000 mg/L of composition. Preferably, Lacto-N-tetraose may be present in said nutritional composition in amount of from 250 to 3000 mg/L, from 300 to 1400 mg/L. from 400 to 1300 mg/L, from 490 to 1215 mg/L, from 500 to 1138 mg/L, from 504 to 1060 mg/L, from 515 to 1000 mg/L, from 600 to 850 mg/L, from 700 to 800 mg/L, from 730 to 750 mg/L, or from 735 to 741 mg/L of composition.

Age-Tailored Nutritional Composition System

For the first time the present inventors developed a nutritional composition system that mimics the changing levels of HMOs in human breast milk, which were previously reported to decrease over time within the lactation period. In particular, this novel nutritional composition system of the invention provides a unique means for mimicking the decrease in HMO levels in the early stages of infant development, i.e. in the first days, weeks and months after infants' birth.

Therefore, preferably, the individual nutritional compositions of the invention differ from each other in the amount of HMOs present therein.

In particular, the age-tailored nutritional composition system of the invention comprises at least one nutritional composition A for infants from 0 up to 1 month of age, and at least one nutritional composition B for infants above 1 month and up to 2 months of age, wherein said nutritional compositions A and B differ from each other in the amount of HMOs present therein.

Since the amount of HMOs in human milk decreases over time, the amount of HMOs present in the at least one nutritional composition A preferably exceeds the amount of HMOs present in the at least one nutritional composition B.

In the context with the present nutritional composition system, the expression "at least one nutritional composition" means that said system may comprise more than one of a particular nutritional composition. For instance, "at least one nutritional composition A" means that the system may comprise from 1 to 100, from 2 to 50, from 4 to 30, from 5 to 20, from 6 to 10 individual compositions A, or from 1 to 10, from 1 to 8, from 1 to 6, from 1 to 4, from 1 to 3 individual compositions A, such as 1, 2, 3, 4, 5, 6, 7, 8, 9, 10 or more nutritional compositions A. Accordingly, "at least one nutritional composition B" means that the system may comprise for example from 1 to 100, from 2 to 50, from 4 to 30, from 5 to 20, from 6 to 10 individual compositions B, or from 1 to 10, from 1 to 8, from 1 to 6, from 1 to 4, from 1 to 3 individual compositions B, and "at least one nutritional composition C" means that the system may comprise from 1 to 100, from 2 to 50, from 4 to 30, from 5 to 20, from 6 to 10 individual compositions C, or from 1 to 10, from 1 to 8, from 1 to 6, from 1 to 4, from 1 to 3 individual compositions C. The same applies to compositions A1, A2, A3, D, E, F, etc.

Typically, the amounts of HMOs present in each nutritional composition A and B are selected according to the age of the infants.

For instance, the amount of HMOs in the at least one nutritional composition A is selected such that it reflects the HMOs profile in human milk during the first month of breast feeding and is thus particularly adapted to the nutritional requirements of newly born infants from 0 and up to 1 month of age. Accordingly, the amount of HMOs in the at least one nutritional composition B is typically selected such that it reflects the HMOs profile in human milk during the second month of breast feeding and is thus adapted to the nutritional requirements of infants above 1 month and up to 2 months of age.

The present age-tailored nutritional composition system is therefore adapted to the HMOs requirements of the developing infant and provides the "right concentration" of HMOs "at the right time".

When referring to a nutritional composition for infants of a certain period of age, this may mean that this nutritional composition is age-tailored; that it addresses the needs of the infants for this specific period of age; that it is adapted for the needs of the infants for this specific period of age; that it is intended to be administered (or fed or given) to infants of this period of age; that it is to be administered (or fed or given) to infants of this period of age and/or that it will be administered (or fed or given) to infants of this period of age.

Advantageously, such adaption of the HMO dosage to the needs of infants of the given age avoids overdosing of HMOs, thus reducing the risk of side effects associated with those ingredients such as gastrointestinal symptoms. Moreover, said adaptation of the HMOs dosage over time enables an optimal supply with these compounds over the entire infant phase and thus stimulates the healthy development of infants in their first year of life.

Preferably, the age-tailored nutritional composition system of the invention further comprises at least one HMOs-containing nutritional composition C for infants above 2 months and up to 4 months of age.

Typically, said at least one composition C differs from compositions A and B in the amount of HMOs present therein.

Since the amount of HMOs in human milk was found to further decrease from the second to the fourth month after infants' birth, the amount of HMOs present in the at least one composition C is preferably lower than the amounts of HMOs present in each of the at least one nutritional composition A and the at least one nutritional composition B.

As in nutritional composition A and B, the amounts of HMOs present in composition C are preferably selected according to the age of the infants. Typically, said amounts are selected such that they reflect the HMOs profile in human milk from the second and up to the fourth months of breast feeding. Thus, including the third nutritional composition C into the age-tailored nutritional composition system of the invention may provide a still enhanced adaptation of this system to the evolving HMOs requirements of the developing infant.

Typically, the at least one nutritional composition A for infants from 0 up to 1 month of age may comprise HMOs in an amount of from 1000 to 10000 mg/L, preferably from 1500 to 8000 mg/L, more preferably from 2000 to 5000 mg/L of said composition, even more preferably in an amount of from 3000 to 4000 mg/L, even more preferably from 3590 to 3673 mg/L, and most preferably in an amount of 3632 mg/L of said composition.

More specifically, the at least one composition A may comprise 2'Fucosyllactose in an amount of from 500 to 5000 mg/L, preferably from 900 to 4000 mg/L, more preferably from 1000 to 2000 mg/L, even more preferably from 1300 to 1700 mg/L, more preferably from 1450 to 1520 mg/L, most preferably 1484 mg/L of composition; 3'Sialyllactose in an amount of from 200 to 280 mg/L, preferably from 210 to 250 mg/L, more preferably from 225 to 240 mg/L, most preferably 231 mg/L of composition; 6'Sialyllactose in an amount of from 450 to 650 mg/L, preferably from 500 to 600 mg/L, more preferably from 530 to 550 mg/L, most preferably 540 mg/L of composition; Lacto-N-neotetraose in an amount of from 150 to 350 mg/L, preferably from 200 to 280 mg/L, more preferably from 220 to 255 mg/L, most preferably 239 mg/L of composition; and/or Lacto-N-tetraose in an amount of from 600 to 4000 mg/L, preferably from 700 to 3000 mg/L, more preferably from 800 to 1400 mg/L, even more preferably from 1000 to 1300 mg/L, even more preferably from 1060 to 1215 mg/L, most preferably 1138 mg/L of composition.

In a preferred embodiment, the at least one composition A comprises a HMOs blend comprising 2'Fucosyllactose, 3'Sialyllactose, 6'Sialyllactose, Lacto-N-neotetraose and Lacto-N-tetraose. It is particularly preferred that said blend comprises 2'Fucosyllactose, 3'Sialyllactose, 6'Sialyllactose, Lacto-N-neotetraose and Lacto-N-tetraose in the amounts defined above for composition A.

Further, typically, the at least one nutritional composition B for infants above 1 month and up to 2 months of age may comprise HMOs in an amount of from 1500 to 3500 mg/L of said composition, and preferably from 2000 to 3000 mg/L, more preferably from 2558 to 2602 mg/L, and most preferably in an amount of 2580 mg/L of said composition.

More specifically, the at least one composition B may comprise 2'Fucosyllactose in an amount of from 1000 to 1500 mg/L, preferably from 1100 to 1300 mg/L, more preferably from 1200 to 1210 mg/L, most preferably 1206 mg/L of composition; 3'Sialyllactose in an amount of from 150 to 250 mg/L, preferably from 190 to 230 mg/L, more preferably from 200 to 225 mg/L, most preferably 211 mg/L of composition; 6'Sialyllactose in an amount of from 200 to 350 mg/L, preferably from 250 to 300 mg/L, more preferably from 270 to 280 mg/L, most preferably 275 mg/L of composition; Lacto-N-neotetraose in an amount of from 100 to 200 mg/L, preferably from 120 to 180 mg/L, more preferably from 130 to 165 mg/L, most preferably 148 mg/L of composition; and/or Lacto-N-tetraose in an amount of from 500 to 1000 mg/L, preferably from 600 to 850 mg/L, more preferably from 730 to 750 mg/L, most preferably 741 mg/L of composition.

In a preferred embodiment, the at least one composition B comprises a HMOs blend comprising 2'Fucosyllactose, 3'Sialyllactose, 6'Sialyllactose, Lacto-N-neotetraose and Lacto-N-tetraose. It is particularly preferred that said blend comprises 2'Fucosyllactose, 3'Sialyllactose, 6'Sialyllactose, Lacto-N-neotetraose and Lacto-N-tetraose in the amounts defined above for composition B.

In case that the age-tailored nutritional composition system of the invention further comprises at least one HMOs-containing nutritional composition C for infants above 2 months and up to 4 months of age, said at least one composition C comprises HMOs in an amount of from 500 to 2500 mg/L, preferably from 1500 to 2000 mg/L, more preferably from 1863 to 1902 mg/L, and most preferably in an amount of 1883 mg/L of composition C.

More specifically, the at least one composition C may comprise 2'Fucosyllactose in an amount of from 800 to 1200 mg/L, preferably from 900 to 1000 mg/L, more preferably from 920 to 980 mg/L, most preferably 949 mg/L of composition; 3'Sialyllactose in an amount of from 150 to 250 mg/L preferably from 180 to 220 mg/L, more preferably from 200 to 210 mg/L, most preferably 205 mg/L of composition; 6'Sialyllactose in an amount of from 80 to 180 mg/L, preferably from 100 to 150 mg/L, more preferably from 125 to 135 mg/L, most preferably 130 mg/L of composition; Lacto-N-neotetraose in an amount of from 50 to 150 mg/L, preferably from 70 to 120 mg/L, more preferably from 80 to 110 mg/L, most preferably 95 mg/L of composition; and/or Lacto-N-tetraose in an amount of from 300 to 700 mg/L, preferably from 400 to 600 mg/L, more preferably from 490 to 515 mg/L, most preferably 504 mg/L of composition.

In a preferred embodiment, the at least one composition C comprises a HMOs blend of 2'Fucosyllactose, 3'Sialyllactose, 6'Sialyllactose, Lacto-N-neotetraose and Lacto-N-tetraose. It is particularly preferred that said blend comprises 2'Fucosyllactose, 3'Sialyllactose, 6'Sialyllactose, Lacto-N-neotetraose and Lacto-N-tetraose in the amounts defined above for composition C.

In a further particularly preferred embodiment, the age-tailored nutritional composition system of the invention comprises a first, second and third nutritional compositions A, B and C, respectively.

There may also be at least one nutritional composition D for infants above 4 months of age, and, optionally, any further nutritional compositions E, F, etc. Also this at least one nutritional composition D and the optional further nutritional compositions (E, F, etc.) may comprise HMOs, wherein the at least one composition D and the optional further nutritional compositions (E, F, etc.) preferably differ from nutritional compositions A, B and C in the amount of HMOs present therein.

As in nutritional composition A, B and C the amounts of HMOs present in the at least one composition D are preferably selected according to the age of the infants. Typically, said amounts are selected such that they reflect the HMOs profile in human milk from the fourth months of breast feeding up to the end of the lactation period, and preferably the fourth months of breast feeding up to 5, 6, 7, 8, 9, 10, 11, or 12 months of breast feeding.

Also, the amounts of HMOs present in each one of the optional further compositions E, F, etc., are preferably selected according to the age of the infants and, typically, such that they reflect the HMOs profile in human milk from the fourth months of breast feeding up to the end of the lactation period, more preferably from 5 months of breast feeding up to 6, 7, 8, 9, 10, 11, or 12 months of breast feeding, and most preferably from 5 up to 12 months, from 6 up to 11 months, from 7 up to 10 months, or from 8 up to 9 months of breast feeding.

Since the amount of HMOs in human breast milk was found to further decrease from the fourth month after infants' birth to the end of the lactation period, e.g. up to 6, 7, 8, 9, 10, 11, or 12 months of breast feeding, the amount of HMOs present in the at least one nutritional composition D and, optionally, in any further nutritional compositions E, F, etc. is lower than in any of nutritional compositions A, B and C. It is particularly preferred that the amount of HMOs present in the at least one nutritional composition C exceeds the amount of HMOs present in the at least one nutritional composition D. In those embodiments wherein the nutritional composition system of the invention comprises further nutritional compositions (E, F, etc.), it is preferred that the amount of HMOs present in the at least one nutritional composition D exceeds the amount of HMOs present in the at least one nutritional composition E, the amount of HMOs present in the at least one nutritional composition E exceeds the amount of HMOs present in the at least one nutritional composition F, etc.

Including at least one nutritional composition D and, optionally, further nutritional compositions (E, F, etc.) into the age-tailored nutritional composition system of the invention may provide a still enhanced adaptation of this system to the evolving HMOs requirements of the developing infant.

A still further adaptation to these requirements may be achieved by providing two nutritional compositions A for infants from 0 up to 1 month of age, namely a first nutritional composition A1 for the first 3 to 7 days after infant's birth and a second nutritional composition A2 for the remaining period of up to 1 month after birth. For instance, the present nutritional composition system may comprise a first nutritional composition A1 for infants from 0 up to 7 days of age, and a second nutritional composition A2 for infants from 8 days up to 1 month of age.

Alternatively, the present nutritional composition system may comprise a first nutritional composition A1 for infants from 0 up to 6 days of age, and a second nutritional composition A2 for infants from 7 days up to 1 month of age.

As a further alternative, the present nutritional composition system may comprise a first nutritional composition A1 for infants from 0 up to 5 days of age, and a second nutritional composition A2 for infants from 6 days up to 1 month of age.

As a yet further alternative, the present nutritional composition system may comprise a first nutritional composition A1 for infants from 0 up to 4 days of age, and a second nutritional composition A2 for infants from 5 days up to 1 month of age.

As a yet further alternative, the present nutritional composition system may comprise a first nutritional composition A1 for infants from 0 up to 3 days of age, and a second nutritional composition A2 for infants from 4 days up to 1 month of age.

Also, the present nutritional composition system may comprise a first nutritional composition A1 for infants from 0 up to 2 days of age, and a second nutritional composition A2 for infants from 3 days up to 1 month of age, or a first nutritional composition A1 for infants from 0 up to 1 day of age, and a second nutritional composition A2 for infants from 2 days up to 1 month of age.

Typically, both nutritional compositions A1 and A2 comprise HMOs, wherein the amounts of HMOs present in each nutritional composition A1 and A2 are selected according to the age of the infants.

Since it was found that the amount of HMOs in human milk already decreases from the day of birth to 1 month after birth, the nutritional compositions A1 and A2 preferably differ from each other in the amount of HMOs present therein, and typically such that the amount of HMOs present in nutritional composition A1 exceeds the amount of HMOs present in nutritional composition A2. For instance, said first nutritional composition A1 may comprise HMOs in a total amount of from 5000 to 10000 mg/L, and preferably from 5000 to 8000 mg/L of composition, whereas the second nutritional composition A2 may comprise HMOs in a total amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition.

In another particular embodiment, the present nutritional composition system may comprise a first nutritional composition A1 for infants from 0 up to 5 days, a second nutritional composition A2 for infants from 6 up to 15 days and a third nutritional composition A3 for infants for the rest of the time period up to 1 month of age (i.e. from 16 days up to 30 or 31 days). These nutritional compositions A1, A2 and A3 preferably comprise human milk oligosaccharides (HMOs), wherein, preferably, the amounts of HMOs present in each nutritional composition A1, A2 and A3 are selected according to the age of the infants. More preferably, nutritional compositions A1, A2 and A3 differ from each other in the amount of HMOs present therein. It is particularly preferred that the amount of HMOs present in nutritional composition A1 exceeds the amount of HMOs present in nutritional composition A2, and that the amount of HMOs present in nutritional composition A2 exceeds the amount of HMOs present in nutritional composition A3. Said first nutritional composition A1 may preferably comprise HMOs in a total amount of from 5000 to 10000 mg/L, and more preferably from 5000 to 8000 mg/L of composition. The second nutritional composition A2 may preferably comprise HMOs in a total amount of from 1000 to 5000 mg/L, preferably from 1500 to 4000 mg/L, more preferably from 2000 to 3673 mg/L, even more preferably from 3000 to 3632 mg/L, and most preferably of 3590 mg/L of composition. The third nutritional composition A3 may preferably comprise HMOs in a total amount of from 500 to 4500 mg/L, preferably from 1000 to 4000 mg/L, more preferably from 2000 to 3500 mg/L, more preferably from 3000 to 3500 mg/L of the composition.

Advantageously, each of these nutritional compositions A (e.g. A1, A2, A3), B, C, D, E, F, etc., comprises a HMOs blend comprising 2'Fucosyllactose, 3'Sialyllactose, 6'Sialyllactose, Lacto-N-neotetraose and Lacto-N-tetraose in the amounts given above. Thus, the evolution of HMOs levels in human milk over time is reproduced by the age-tailored nutritional composition system of the invention as closely as possible.

Typically, the individual nutritional compositions A (e.g. A1, A2, A3), B, C, D, E, F, etc. are in the form of infant formulae, wherein these infant formulae can be either a complete or a partial substitute for human milk.

Infant Nutrition Kit

In a further embodiment, the present nutritional composition system may be in the form of an infant nutrition kit. Preferably, said kit comprises a set of age-tailored nutritional compositions according to the invention.

For instance, such a kit may comprise a set of the nutritional composition A of the invention in a quantity that is sufficient for feeding a newly born infant from its birth and up to 1 month of age.

Alternatively, or in addition, the kit may comprise a set of the nutritional composition B of the invention in a quantity that is sufficient for feeding an infant from 1 month and up to 2 months of age.

Alternatively, or in addition, the kit may further comprise a set of the nutritional composition C of the invention in a quantity that is sufficient for feeding an infant from 2 months and up to 4 month of age.

In a preferred embodiment, the present infant nutrition kit comprises a combination of a set of the nutritional composition A and a set of the nutritional composition B as defined above. Even more preferably, said kit further comprises a set of the nutritional composition C as defined above. Thus, the infant nutrition kit provides an age-tailored nutritional composition system for infants, which is specifically adapted to the evolving nutritional needs of these infants from 0 and up to 4 months of age.

The kit may further comprise a set of the nutritional composition D of the invention in a quantity that is sufficient for feeding an infant from 4 month and up to 5, 6, 7, 8, 9, 10, 11, or 12 months of age. Optionally, said kit may comprise any further nutritional compositions E, F, etc. in a quantity that is sufficient for feeding an infant from four months of age up to 6, 7, 8, 9, 10, 11, or 12 months of age, and preferably from 5 up to 12 months, from 6 up to 11 months, from 7 up to 10 months, from 8 up to 9 months of age.

In a particular embodiment, the infant nutrition kit of the invention comprises two nutritional compositions A, namely the first nutritional composition A1 and the second nutritional composition A2 as described above.

The first nutritional composition A1 may be comprised in the present infant nutrition kit in a quantity that is sufficient for feeding an infant from its birth up to the first 3 to 7 days after birth and the second nutritional composition A2 may be comprised in said kit in a quantity that is sufficient for feeding said infant for the remaining period of up to 1 month after birth.

In another particular embodiment, the infant nutrition kit of the invention comprises three nutritional compositions A as described above, namely a first nutritional composition A1 for infants from 0 up to 5 days, a second nutritional composition A2 for infants from 6 up to 15 days and a third nutritional composition A3 for infants for the rest of the time period up to 1 month of age (i.e. from 16 days up to 30 or 31 days).

Typically, the individual age-tailored nutritional compositions of the kit are in the form of infant formulae, wherein these infant formulae can be either a complete or a partial substitute for human milk.

The set of age-tailored nutritional compositions of the kit may be packed in single dose units, preferably wherein each single dose unit comprises a sufficient amount of nutritional composition to prepare a single serving upon reconstitution with water.

Typically, said single dose units comprise 10 to 30 g of powdered nutritional composition or 1 to 50 mL of a concentrate of nutritional composition. Preferably the single dose units are in the form of capsules. For instance, suitable capsules are described in WO2010/128051, WO2010/128031, WO2010/128028 and WO2014/082924. The capsules may be disposable capsules equipped with opening means contained within the capsule to permit draining of the reconstituted formula directly from the capsule into a receiving vessel. The receiving vessel can be for example a feeding bottle for the infant. A method of using capsules for dispensing an infant nutritional composition is described in WO2006/077259.

In a preferred embodiment, the capsules may be specifically designed for insertion into a beverage production machine such as an infant formula production machine. Suitable capsules and machines are for example described in WO2012/034819, WO2012/062842, WO2012/104173 and WO2012/146470.

The single dose units may also be in the form of stick packs (blister packs) or sachets.

The individual nutritional compositions being part of the infant nutrition kit of the invention may be packed into individual capsules and presented to the consumer in multipacks containing a sufficient number of capsules to meet the requirements of an infant over a period of time, e.g. one week or one month.

For instance, the kit may comprise a certain quantity of single dose units comprising a sufficient amount of nutritional composition A, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition A.

Alternatively, or in addition, the kit may comprise a certain quantity of single dose units comprising a sufficient amount of nutritional composition B, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition B.

Alternatively, or in addition, the kit may also comprise a certain quantity of single dose units comprising a sufficient amount of nutritional composition C, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition C.

Alternatively, or in addition, the kit may also comprise a certain quantity of single dose units comprising a sufficient amount of nutritional composition A1, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition A1.

Alternatively, or in addition, the kit may also comprise a certain quantity of single dose units comprising a sufficient amount of nutritional composition A2, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition A2.

Alternatively, or in addition, the kit may also comprise a certain quantity of single dose units comprising a sufficient amount of nutritional composition A3, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition A3.

Alternatively, or in addition, the kit may also comprise a certain quantity of single dose units comprising a sufficient amount of nutritional composition D or E or F, etc. in the above-named amounts.

Use of the Age-Tailored Nutritional Composition System

The present age-tailored nutritional composition system or the present infant nutrition kit may be particularly used for feeding an infant, thereby providing a suitable nutrition to said infant.

The age-tailored nutritional composition system or the infant nutrition kit comprising a set of age-tailored nutritional compositions of the invention may be further used in providing a health benefit to infants.

For instance, the age-tailored nutritional composition system or the infant nutrition kit of the invention may be used for the following: treating or preventing diarrhea, treating or preventing gut discomfort, weaning facilitation, maturation of the immune system, preventing or managing allergy, reducing cardiovascular diseases later in life, reducing risk of obesity, reducing risk of infections, ensuring a normal growth curve, improving or insuring optimal cognition, improving immune function and immune defenses, or preventing upper respiratory tract infections like otitis media or common cold.

Method for the Manufacture of a Set of Nutritional Compositions for Infants

The invention further relates to a method for the manufacture of a set of nutritional compositions for infants.

In a first step of this method, at least one nutritional composition is prepared, which is specifically adapted to the nutritional needs of infants from 0 up to 1 month of age (composition A). In the same step, the method comprises preparing at least one other nutritional composition which is specifically adapted to the nutritional needs of infants above 1 month and up to 2 months of age (composition B).

It is preferred that in this first step of the method at least one further nutritional composition is prepared which is specifically adapted to the nutritional needs of infants above 2 months and up to 4 months of age (composition C).

The nutritional compositions may be manufactured in any suitable manner. For example, the nutritional compositions may be prepared by blending together a protein source, a carbohydrate source, and a fat source in appropriate proportions. If used, emulsifiers may be included in the blend. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C. for example by flash cooling. The liquid mixture may then be homogenised for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture are conveniently standardised at this point. The homogenised mixture may be transferred to a suitable drying apparatus such as a spray drier or freeze drier and converted to powder. The powder should have a moisture content of less than about 3% by weight. Alternatively, the homogenized mixture is concentrated.

In a second step of the present manufacturing method, an amount of HMOs is selected for each of the nutritional compositions A and B according to the age of the infants.

In a preferred embodiment, the second step of the method further comprises selecting an amount of HMOs for the at least one further nutritional composition C according to the age of the infants.

In a particularly preferred embodiment, an amount of HMOs is selected for each of the compositions A, B and C, such that these nutritional compositions differ from each other in the amount of HMOs present therein.

More preferably, the amount of HMOs is selected for the at least one nutritional composition A such that it exceeds the amount of HMOs that is selected for the at least one nutritional composition B, and, optionally, the amount of HMOs is selected for the at least one composition B such that it exceeds the amount of HMOs that is selected for the at least one nutritional composition C.

In an embodiment, the first step of the present method further comprises preparing at least one further nutritional composition, which is specifically adapted to the nutritional needs of infants above 4 months of age, such as for example to the nutritional needs of infants from 4 months of age up to 5, 6, 7, 8, 9, 10, 11, or 12 months of age (composition D).

In this embodiment, the second step of the method may further comprise selecting an amount of HMOs for the at least one further nutritional composition D according to the age of the infants, wherein this amount preferably differs from the amount of HMOs selected for each one of compositions A, B and C, more preferably such that the amount selected for each one of compositions A, B and C exceeds the amount selected for nutritional composition D.

The first step of the present method may further comprise preparing further nutritional compositions that are specifically adapted to the nutritional needs of infants above 4 months of age, and preferably to the nutritional needs of infants from 5 up to 12 months, from 6 up to 11 months, from 7 up to 10 months, from 8 up to 9 months of age (compositions E, F, etc.). In this case, the second step of the method may further comprise selecting an amount of HMOs for each one of the further nutritional compositions E, F, etc. according to the age of the infants, wherein these amounts preferably differ from each other and also differ from the amount of HMOs selected for each one of compositions A, B, C and D, more preferably such that the amount selected for each one of compositions A, B, C and D, exceeds the amount selected for nutritional composition E, the amount selected for compositions E, exceeds the amount selected for nutritional composition F, the amount selected for compositions F exceeds the amount selected for nutritional composition G, etc.

In another specific embodiment, the first step of preparing at least one nutritional composition adapted to the nutritional needs of infants from 0 up to 1 month of age (composition A) comprises preparing two different nutritional compositions, namely a first nutritional composition, which is specifically adapted to the nutritional needs of infants from the first 3 to 7 days of age (composition A1) and a second nutritional composition which is specifically adapted to the nutritional needs of infants in the remaining period up to 1 month of age (composition A2).

Also in this specific embodiment, the second step of the method further comprises selecting an amount of HMOs for each of the nutritional compositions A1 and A2 according to the age of the infants, more preferably wherein said amount of HMOs is selected such that nutritional compositions A1 and A2 differ from each other in the amount of HMOs present therein. It is particularly preferred that for each of nutritional compositions A1 and A2 the amount of HMOs is selected such that the amount of HMOs selected for nutritional composition A1 exceeds the amount of HMOs selected for nutritional composition A2.

More specifically, HMOs may be selected for any of the above nutritional compositions in a total amount of from 500 to 10000 mg/L, preferably from 1000 to 8000 mg/L, from 1500 to 5000 mg/L or from 1800 to 4000 mg/L of composition. Preferably the HMOs are present in a nutritional composition in a total amount of from 1863 to 3673 mg/L, from 1883 to 3632 mg/L, from 1902 to 3590 mg/L, from 2000 to 3500 mg/L, from 2500 to 3000 mg/L, from 2558 to 2602 mg/L or in an amount of 2580 mg/L of composition, depending on the age of the infants.

In the present method, the HMOs may be particularly selected from "sialylated oligosaccharides", "fucosylated oligosaccharides", "N-acetylated oligosaccharides" or any mixtures thereof, and preferably from HMOs which are naturally present in human breast milk such as 2'Fucosyllactose (2'FL or 2FL or 2-FL), 3'Sialyllactose (3'SL or 3SL or 3-SL), 6'Sialyllactose (6'SL or 6SL or 6-SL), Lacto-N-neotetraose (LNnT), Lacto-N-tetraose (LNT), or any combination thereof.

In a third step of the present method, the amount of HMOs selected in the second step of said method is incorporated into the corresponding nutritional composition. The HMOs may be added to the powdered nutritional compositions prepared in the first step by dry mixing.

Alternatively, the HMOs may be added at an earlier stage during preparation of the nutritional compositions, for example by blending together with the protein source, carbohydrate source, and fat source. A skilled person is able to determine when the incorporation of the HMOs into the nutritional compositions should occur.

For instance, in an alternative embodiment, the method of the invention may comprise a first step of selecting an amount of HMOs according to the specific HMOs requirements of infants from 0 up to 1 month of age, and selecting an amount of HMOs according to the specific HMOs requirements of infants above 1 month and up to 2 months of age.

Preferably, in this first step of the method, a further amount of HMOs is selected according to the specific HMOs requirements of infants above 2 months and up to 4 months of age.

In a second step of this alternative embodiment, the amount of HMOs selected according to the specific HMOs requirements of infants from 0 up to 1 month of age is blended together with at least a protein source, a carbohydrate source and a fat source, in order to provide a nutritional composition A for infants from 0 up to 1 month of age. Preferably, the amounts of the protein source, the carbohydrate source, and the fat source are specifically adapted to the nutritional needs of infants from 0 up to 1 month of age, In the same step, the amount of HMOs selected according to the specific HMOs requirements of infants above 1 month and up to 2 months of age is blended together with at least a protein source, a carbohydrate source and a fat source to provide a nutritional composition B for infants above 1 month and up to 2 months of age. Preferably, the amounts of the protein source, the carbohydrate source, and the fat source are specifically adapted to the nutritional needs of infants above 1 month and up to 2 months of age, Preferably, the same step comprises blending the amount of HMOs selected according to the specific HMOs requirements of infants above 2 months and up to 4 months of age together with at least a protein source, a carbohydrate source and a fat source to provide a nutritional composition C for infants above 2 months and up to 4 months of age. Preferably, the amounts of the protein source, the carbohydrate source, and the fat source are specifically adapted to the nutritional needs of infants above 2 months and up to 4 months of age, Optionally, the first step of the alternative embodiment further comprises selecting an amount of HMOs according to the specific HMOs requirements of infants above 4 months of age, such as for example to the specific HMOs requirements of infants from 4 up to 5, 6, 7, 8, 9, 10, 11, or 12 months of age. Then, the second step of the method comprises blending the amount of HMOs selected according to the specific HMOs requirements of infants from 4 up to 5, 6, 7, 8, 9, 10, 11, or 12 months of age together with at least a protein source, a carbohydrate source and a fat source to provide a nutritional composition D for infants from 4 up to 5, 6, 7, 8, 9, 10, 11, or 12 months of age. Preferably, the amounts of the protein source, the carbohydrate source, and the fat source are specifically adapted to the nutritional needs of infants from 4 up to 5, 6, 7, 8, 9, 10, 11, or 12 months of age, The first step of the alternative embodiment may also comprise selecting further amounts of HMOs according to the specific HMOs requirements of infants above 4 months of age, and preferably according to the specific HMOs requirements of infants from 5 up to 12 months, from 6 up to 11 months, from 7 up to 10 months, or from 8 up to 9 months of age. In this case, the second step of the method may further comprise blending each of the selected HMOs amounts together with at least a protein source, a carbohydrate source and a fat source to provide any further nutritional composition E, F, etc. for infants above 4 months of age, and preferably for infants from 5 up to 12 months, from 6 up to 11 months, from 7 up to 10 months, from 8 up to 9 months of age. Preferably, the amounts of the protein source, the carbohydrate source, and the fat source are specifically adapted to the nutritional needs of infants having the respective age.

The first step of the alternative embodiment may also comprise selecting two different amounts of HMOs according to the specific HMOs requirements of infants from 0 up to 1 month of age. In particular, said first step may comprises selecting a first amount of HMOs according to the specific HMOs requirements of infants for the first 3 to 7 days of age and selecting a second amount of HMOs according to the specific HMOs requirements of infants in the remaining period of up to 1 month of age. Then, in the second step of this embodiment, the amount of HMOs selected according to the specific HMOs requirements of infants for the first 3 to 7 days of age is blended together with at least a protein source, a carbohydrate source, and a fat source, to provide a nutritional composition A1 for infants between the first 3 to 7 days of age and the amount of HMOs selected according to the specific HMOs requirements of infants in the remaining period of up to 1 month of age is blended together with at least a protein source, a carbohydrate source, and a fat source, to provide a nutritional composition A2 for infants in the remaining period of up to 1 month of age. Preferably, the amounts of the protein source, the carbohydrate source, and the fat source are specifically adapted to the nutritional needs of infants for the first 3 to 7 days of age and of infants in the remaining period of up to 1 month of age, respectively.

The nutritional composition blends may be further processed as described above. For instance, emulsifiers, vitamins, minerals and water may be included in the blend to form a liquid mixture. The liquid mixture may then be thermally treated, cooled, homogenised and dried or concentrated as described above.

In this alternative embodiment the amounts of HMOs may be selected according to the age of the infant as described herein, and preferably in the amounts described herein.

Most preferably, the nutritional compositions A (e.g. A1, A2), B, C, D, E, etc. prepared by the present methods correspond to the nutritional compositions A (e.g. A1, A2), B, C, D, E, etc of the age-tailored nutritional composition system according to the invention.

Infant Nutrition Regimen

The invention further relates to an infant nutrition regimen. The infant nutrition regimen comprises feeding an infant from 0 up to 1 month of age at least one nutritional composition A comprising HMOs.

The infant nutrition regimen further comprises feeding the same infant above 1 month and up to 2 months of age at least one nutritional composition B comprising HMOs. Both compositions A and B preferably differ from each other in the amount of HMOs present therein.

Advantageously, the infant nutrition regimen further comprises feeding the same infant above 2 months and up to 4 months of age at least one nutritional composition C. Preferably, also this nutritional composition C comprises HMOs.

It is also preferred that the nutritional compositions A, B and C differ from each other in the amount of HMOs present therein, more preferably such that the amount of HMOs present in the at least one nutritional composition A exceeds the amount of HMOs present in the at least one nutritional composition B and the amount of HMOs present in the at least one nutritional composition B exceeds the amount of HMOs present in the at least one nutritional composition C, if applicable.

The present infant nutrition regimen may further comprise feeding an infant above 4 months of age at least one nutritional composition D, and, optionally, any further nutritional compositions E, F, etc. Also this at least one nutritional composition D and the optional further nutritional compositions (E, F, etc.), may comprise HMOs, wherein the at least one composition D and the optional further nutritional compositions (E, F, etc.) preferably differ from nutritional compositions A, B and C in the amount of HMOs present therein. It is particularly preferred that the amount of HMOs present in the at least one nutritional composition C exceeds the amount of HMOs present in the at least one nutritional composition D. In those embodiments wherein the nutritional composition system of the invention comprises further nutritional compositions E, F, etc., it is preferred that the amount of HMOs present in the at least one nutritional composition D exceeds the amount of HMOs present in the at least one nutritional composition E, the amount of HMOs present in the at least one nutritional composition E exceeds the amount of HMOs present in the at least one nutritional composition F, etc.

In a particular embodiment, the infant nutrition regimen may comprise feeding an infant from 0 up to 1 month two nutritional compositions A, namely a first nutritional composition A1 and a second nutritional composition A2. Preferably, the first nutritional composition A1 is fed to said infant for the first 3 to 7 days after infant's birth and the second nutritional composition A2 is fed to said infant for the remaining period of up to 1 month after birth in a sequential manner.

Typically, both nutritional compositions A1 and A2 comprise HMOs, wherein the amounts of HMOs present in each nutritional composition A1 and A2 are selected according to the age of the infants. More typically, the nutritional compositions A1 and A2 differ from each other in the amount of HMOs present therein such that preferably the amount of HMOs present in nutritional composition A1 exceeds the amount of HMOs present in nutritional composition A2.

In another particular embodiment, the infant nutrition regimen may comprise feeding an infant from 0 up to 1 month three nutritional compositions A, namely a first nutritional composition A1, a second nutritional composition A2 and a third nutritional composition A3. Preferably the first nutritional composition A1 is fed to infants from 0 up to 5 days, the second nutritional composition A2 is fed to infants from 6 up to 15 days and the third nutritional composition A3 is fed to infants for the rest of the time period up to 1 month of age (i.e. from 16 days up to 30 or 31 days). These nutritional compositions A1, A2 and A3 preferably comprise human milk oligosaccharides (HMOs), wherein, preferably, the amounts of HMOs present in each nutritional composition A1, A2 and A3 are selected according to the age of the infants. More preferably, nutritional compositions A1, A2 and A3 differ from each other in the amount of HMOs present therein. It is particularly preferred that the amount of HMOs present in nutritional composition A1 exceeds the amount of HMOs present in nutritional composition A2, and that the amount of HMOs present in nutritional composition A2 exceeds the amount of HMOs present in nutritional composition A3.

The HMOs comprised in nutritional compositions A (e.g. A1, A2, A3), B, C, D, E, etc. of the infant nutrition regimen are preferably selected from "sialylated oligosaccharides", "fucosylated oligosaccharides", "N-acetylated oligosaccharides" or any mixtures thereof, more preferably from 2'Fucosyllactose (2'FL or 2FL or 2-FL), 3'Sialyllactose (3'SL or 3SL or 3-SL), 6'Sialyllactose (6'SL or 6SL or 6-SL), Lacto-N-neotetraose (LNnT), Lacto-N-tetraose (LNT), or any combination thereof.

Most preferably, said nutritional compositions A (e.g. A1, A2, A3), B, C, D, E, etc. of the infant nutrition regimen correspond to nutritional compositions A (e.g. A1, A2, A3), B, C, D, E, etc. disclosed herein.

These different nutritional compositions A (e.g. A1, A2, A3), B, C, D, E, etc. are sequentially administered and there is no overlap of times of administration of the different nutritional compositions A (e.g. A1, A2, A3), B, C, D, E, etc.

The compositions can also be administered during the entire specific window of time, or during only a part thereof, and the administration can be continuous or not.

In addition to these nutritional compositions of the invention the infant nutrition regimen may include feeding the infants with complementary foods. The complementary foods may be any of the foods commercially available for the corresponding age range. These complementary foods can be for example pureed vegetables, meats, fish, fruits.

Preferably, the nutritional compositions of the invention fed to the infants constitute more than half of the meals of these infants.

It has been found that by adapting to the changing nutritional needs of infants during their first four months after birth, the present invention provides numerous health benefits which have not been achieved by the sets of nutritional compositions known in the art.

Method for Providing Nutrition to an Infant

The invention further relates to a method for providing nutrition to an infant.

This method may comprise:
 feeding an infant from 0 up to 1 month of age at least one nutritional composition A,
 feeding said infant above 1 month and up to 2 months of age at least one nutritional composition B;
wherein the nutritional compositions A and B comprise HMOs and wherein said nutritional compositions A and B differ from each other in the amount of HMOs present therein.

It may further comprise:
 feeding said infant above 2 months and up to 4 months of age at least one nutritional composition C;
preferably wherein the at least one nutritional composition C comprises HMOs;
 and more preferably wherein the nutritional compositions A, B and C differ from each other in the amount of HMOs present therein.

The specific details and embodiments developed in the framework of the other aspects, especially for the seventh aspect about the infant regimen, apply similarly on this method.

The present invention is further illustrated herein by means of the following non-limiting examples.

EXAMPLES

Example 1: Age-Tailored Set of Nutritional Compositions

An age-tailored set of nutritional compositions is given in Table 1 below:

TABLE 1

| | | Composition | | | |
| --- | --- | --- | --- | --- | --- |
| | | A | B | C | D |
| | | Age range | | | |
| | | 0 up to 1 month | 1 up to 2 months | 2 up to 4 months | Above 4 months |
| Basics | Reconstitution RTD Volume (ml) | 100 to 200 | 100 to 200 | 100 to 200 | 100 to 200 |

TABLE 1-continued

|  |  | Composition | | | |
|---|---|---|---|---|---|
|  |  | A | B | C | D |
|  |  | Age range | | | |
|  |  | 0 up to 1 month | 1 up to 2 months | 2 up to 4 months | Above 4 months |
|  | Energy density (kcal/100 ml) | 63-67 | 63-67 | 63-67 | 63-67 |
|  | Content (g/100 kcal) | 1.8-2.25 | 1.8-2.25 | 1.8-2.25 | 1.8-2.25 |
| Protein | Content (g/l) | 11.3-15.1 | 11.3-15.1 | 11.3-15.1 | 11.3-15.1 |
|  | Whey:Casein | 70:30 | 70:30 | 70:30 | 70:30 |
|  | Type | Lactose | Lactose | Lactose | Lactose |
| Carbohydrates | Content (g/100 kcal) | 9.7 to 11.6 | 9.7 to 11.6 | 9.7 to 11.6 | 9.7 to 11.6 |
|  | Content (g/l) | 65.0 to 73.5 | 65.0 to 73.5 | 65.0 to 73.5 | 65.0 to 73.5 |
| Lipids | Type | Milk & Veg. | Milk & Veg. | Milk & Veg. | Milk & Veg. |
|  | Content (g/100 kcal) | 5.1 to 5.8 | 5.1 to 5.8 | 5.1 to 5.8 | 5.1 to 5.8 |
|  | content (as % of total energy) | 45.9 to 52.2 | 45.9 to 52.2 | 45.9 to 52.2 | 45.9 to 52.2 |
|  | Content (g/l) | 32.1 to 38.9 | 32.1 to 38.9 | 32.1 to 38.9 | 32.1 to 38.9 |
|  | LC-PUFA | DHA + ARA | DHA + ARA | DHA + ARA | DHA + ARA |
| Probiotics | Type | *B. lactis* CNCM I-3446 and/or *B. longum* CNCM I-2618 | *B. lactis* CNCM I-3446 and/or *B. longum* CNCM I-2618 | *B. lactis* CNCM I-3446 and/or *B. longum* CNCM I-2618 | *B. lactis* CNCM I-3446 and/or *B. longum* CNCM I-2618 |
|  | Content | $2 \times 10^5$ cfu/g | $2 \times 10^5$ cfu/g | $2 \times 10^5$ cfu/g | $2 \times 10^5$ cfu/g |
| HMOs (mg/L) | 2'Fucosyllactose | 1484.1 | 1205.6 | 949.4 | <949.4 |
|  | 3'Sialyllactose | 230.5 | 210.5 | 205.2 | <205.2 |
|  | 6'Sialyllactose | 540.5 | 275.1 | 129.7 | <129.7 |
|  | Lacto-N-neotetraose | 239.2 | 147.9 | 95.0 | <95.0 |
|  | Lacto-N-tetraose | 1137.5 | 740.6 | 503.6 | <503.6 |
| Nucleotide | CMP (mg/100 kcal) | 1.1 | 1.1 | 1.1 | 1.1 |
|  | UMP | 0.7 | 0.7 | 0.7 | 0.7 |
|  | AMP | 0.7 | 0.7 | 0.7 | 0.7 |
|  | GMP | 0.2 | 0.2 | 0.2 | 0.2 |
| Minerals (/100 kcal) | Na (mg) | 25 to 37.5 | 25 to 37.5 | 25 to 37.5 | 25 to 37.5 |
|  | K (mg) | 80 to 95 | 80 to 95 | 80 to 95 | 80 to 95 |
|  | Na/K (molar ratio) | 0.53-0.67 | 0.53-0.67 | 0.53-0.67 | 0.53-0.67 |
|  | (Na + K)/Cl molar ratio | 1.71-1.81 | 1.71-1.81 | 1.71-1.81 | 1.71-1.81 |
|  | Cl (mg) | 65 to 80 | 65 to 80 | 65 to 80 | 65 to 80 |
|  | Ca (mg) | 60 | 60 | 60 | 60 |
|  | P (mg) | 33 | 33 | 33 | 33 |
|  | Mg (mg) | 7 | 7 | 7 | 7 |
|  | Mn (µg) | 5 | 5 | 5 | 5 |
|  | Ca/P | 1.8 | 1.8 | 1.8 | 1.8 |
| Vitamins (/100 kcal) | Vit. A (mg RE) | 0.09 to 01125 | 0.09 to 01125 | 0.09 to 01125 | 0.09 to 01125 |
|  | Vit. D (mg) | 0.0015 | 0.0015 | 0.0015 | 0.0015 |
|  | Vit. E (mg) | 1.3 | 1.3 | 1.3 | 1.3 |
|  | Vit. K1 (µg) | 8 | 8 | 8 | 8 |
|  | Vit. C (mg) | 15 | 15 | 15 | 15 |
|  | Vit. B1 (mg) | 0.07 to 0.1 | 0.07 to 0.1 | 0.07 to 0.1 | 0.07 to 0.1 |
|  | Vit. B2 (mg) | 0.1 | 0.1 | 0.1 | 0.1 |
|  | Niacin (mg) | 0.5 | 0.5 | 0.5 | 0.5 |
|  | Vit. B6 (mg) | 0.05 | 0.05 | 0.05 | 0.05 |
|  | Folic acid (µg) | 15 to 16 | 15 to 16 | 15 to 16 | 15 to 16 |
|  | Pantothenic Acid (mg) | 0.7 to 0.8 | 0.7 to 0.8 | 0.7 to 0.8 | 0.7 to 0.8 |
|  | Vit. B12 (µg) | 0.2 | 0.2 | 0.2 | 0.2 |
|  | Biotin (µg) | 2 | 2 | 2 | 2 |
|  | Choline (mg) | 20 | 20 | 20 | 20 |
|  | Inositol (mg) | 25 | 25 | 25 | 25 |
|  | Taurine (mg) | 8 | 8 | 8 | 8 |
|  | Carnitine (mg) | 1.5 | 1.5 | 1.5 | 1.5 |

TABLE 1-continued

|  |  | Composition | | | |
|---|---|---|---|---|---|
|  |  | A | B | C | D |
|  |  | Age range | | | |
|  |  | 0 up to 1 month | 1 up to 2 months | 2 up to 4 months | Above 4 months |
| Trace Elements (/100 kcal) | Fe (mg) | 0.7 | 0.7 | 0.7 | 0.7 |
|  | I (µg) | 15 to 20 | 15 to 20 | 15 to 20 | 15 to 20 |
|  | Cu (mg) | 0.06 to 0.08 | 0.06 to 0.08 | 0.06 to 0.08 | 0.06 to 0.08 |
|  | Zn (mg) | 1 to 1.2 | 1 to 1.2 | 1 to 1.2 | 1 to 1.2 |
|  | Se (µg) | 3 to 4 | 3 to 4 | 3 to 4 | 3 to 4 |

* fat mix follows AHA: sat. Fat <7% E + polyuns. <10% E LA/ALA 5.0
** tfa

Example 2: Age-Tailored Set of Nutritional Compositions

An age-tailored set of nutritional compositions is given in Table 2 below:

TABLE 2

|  |  | Composition | | | |
|---|---|---|---|---|---|
|  |  | A | B | C | D |
|  |  | Age range | | | |
|  |  | 0 up to 1 month | 1 up to 2 months | 2 up to 4 months | Above 4 months |
| Basics | Reconstitution RTD Volume (ml) | 100 to 200 | 100 to 200 | 100 to 200 | 100 to 200 |
|  | Energy density (kcal/100 ml) | 63-67 | 63-67 | 63-67 | 63-67 |
|  | Content (g/100 kcal) | 1.8-2.25 | 1.8-2.25 | 1.8-2.25 | 1.8-2.25 |
| Protein | Content (g/l) | 11.3-15.1 | 11.3-15.1 | 11.3-15.1 | 11.3-15.1 |
|  | Whey:Casein | 70:30 | 70:30 | 70:30 | 70:30 |
|  | Type | Lactose | Lactose | Lactose | Lactose |
| Carbohydrates | Content (g/100 kcal) | 9.7 to 11.6 | 9.7 to 11.6 | 9.7 to 11.6 | 9.7 to 11.6 |
|  | Content (g/l) | 65.0 to 73.5 | 65.0 to 73.5 | 65.0 to 73.5 | 65.0 to 73.5 |
| Lipids | Type | Milk & Veg. | Milk & Veg. | Milk & Veg. | Milk & Veg. |
|  | Content (g/100 kcal) | 5.1 to 5.8 | 5.1 to 5.8 | 5.1 to 5.8 | 5.1 to 5.8 |
|  | content (as % of total energy) | 45.9 to 52.2 | 45.9 to 52.2 | 45.9 to 52.2 | 45.9 to 52.2 |
|  | Content (g/l) | 32.1 to 38.9 | 32.1 to 38.9 | 32.1 to 38.9 | 32.1 to 38.9 |
|  | LC-PUFA | DHA + ARA | DHA + ARA | DHA + ARA | DHA + ARA |
| Probiotics | Type | B. lactis CNCM I-3446 and/or B. longum CNCM I-2618 | B. lactis CNCM I-3446 and/or B. longum CNCM I-2618 | B. lactis CNCM I-3446 and/or B. longum CNCM I-2618 | B. lactis CNCM I-3446 and/or B. longum CNCM I-2618 |
|  | Content | $2 \times 10^5$ cfu/g | $2 \times 10^5$ cfu/g | $2 \times 10^5$ cfu/g | $2 \times 10^5$ cfu/g |
| HMOs (mg/L) | 2'Fucosyllactose | 2170.0 | 1764.0 | 1376.0 | <1376.0 |
|  | 3'Sialyllactose | 230.5 | 210.5 | 205.2 | <205.2 |
|  | 6'Sialyllactose | 540.5 | 275.1 | 129.7 | <129.7 |
|  | Lacto-N-neotetraose | 239.2 | 147.9 | 95.0 | <95.0 |
|  | Lacto-N-tetraose | 1137.5 | 740.6 | 503.6 | <503.6 |
| Nucleotide | CMP (mg/100 kcal) | 1.1 | 1.1 | 1.1 | 1.1 |
|  | UMP | 0.7 | 0.7 | 0.7 | 0.7 |
|  | AMP | 0.7 | 0.7 | 0.7 | 0.7 |
|  | GMP | 0.2 | 0.2 | 0.2 | 0.2 |
| Minerals (/100 kcal) | Na (mg) | 25 to 37.5 | 25 to 37.5 | 25 to 37.5 | 25 to 37.5 |
|  | K (mg) | 80 to 95 | 80 to 95 | 80 to 95 | 80 to 95 |
|  | Na/K (molar ratio) | 0.53-0.67 | 0.53-0.67 | 0.53-0.67 | 0.53-0.67 |

TABLE 2-continued

|  |  | Composition | | | |
|---|---|---|---|---|---|
|  |  | A | B | C | D |
|  |  | Age range | | | |
|  |  | 0 up to 1 month | 1 up to 2 months | 2 up to 4 months | Above 4 months |
|  | (Na + K)/Cl molar ratio | 1.71-1.81 | 1.71-1.81 | 1.71-1.81 | 1.71-1.81 |
|  | Cl (mg) | 65 to 80 | 65 to 80 | 65 to 80 | 65 to 80 |
|  | Ca (mg) | 60 | 60 | 60 | 60 |
|  | P (mg) | 33 | 33 | 33 | 33 |
|  | Mg (mg) | 7 | 7 | 7 | 7 |
|  | Mn (μg) | 5 | 5 | 5 | 5 |
|  | Ca/P | 1.8 | 1.8 | 1.8 | 1.8 |
| Vitamins (/100 kcal) | Vit. A (mg RE) | 0.09 to 01125 | 0.09 to 01125 | 0.09 to 01125 | 0.09 to 01125 |
|  | Vit. D (mg) | 0.0015 | 0.0015 | 0.0015 | 0.0015 |
|  | Vit. E (mg) | 1.3 | 1.3 | 1.3 | 1.3 |
|  | Vit. K1 (μg) | 8 | 8 | 8 | 8 |
|  | Vit. C (mg) | 15 | 15 | 15 | 15 |
|  | Vit. B1 (mg) | 0.07 to 0.1 | 0.07 to 0.1 | 0.07 to 0.1 | 0.07 to 0.1 |
|  | Vit. B2 (mg) | 0.1 | 0.1 | 0.1 | 0.1 |
|  | Niacin (mg) | 0.5 | 0.5 | 0.5 | 0.5 |
|  | Vit. B6 (mg) | 0.05 | 0.05 | 0.05 | 0.05 |
|  | Folic acid (μg) | 15 to 16 | 15 to 16 | 15 to 16 | 15 to 16 |
|  | Pantothenic Acid (mg) | 0.7 to 0.8 | 0.7 to 0.8 | 0.7 to 0.8 | 0.7 to 0.8 |
|  | Vit. B12 (μg) | 0.2 | 0.2 | 0.2 | 0.2 |
|  | Biotin (μg) | 2 | 2 | 2 | 2 |
|  | Choline (mg) | 20 | 20 | 20 | 20 |
|  | Inositol (mg) | 25 | 25 | 25 | 25 |
|  | Taurine (mg) | 8 | 8 | 8 | 8 |
|  | Carnitine (mg) | 1.5 | 1.5 | 1.5 | 1.5 |
| Trace Elements (/100 kcal) | Fe (mg) | 0.7 | 0.7 | 0.7 | 0.7 |
|  | I (μg) | 15 to 20 | 15 to 20 | 15 to 20 | 15 to 20 |
|  | Cu (mg) | 0.06 to 0.08 | 0.06 to 0.08 | 0.06 to 0.08 | 0.06 to 0.08 |
|  | Zn (mg) | 1 to 1.2 | 1 to 1.2 | 1 to 1.2 | 1 to 1.2 |
|  | Se (μg) | 3 to 4 | 3 to 4 | 3 to 4 | 3 to 4 |

\* fat mix follows AHA: sat. Fat <7% E + polyuns. <10% E LA/ALA 5.0
\*\* tfa

Having thus described the present invention in detail and the advantages thereof, it is to be understood that the detailed description is not intended to limit the scope of the invention thereof.

Example 3: Clinical Trial on Normal Ranges of Human Milk Oligosaccharides in Breast Milk of Healthy Mothers Study Design An open, single-centre, 1 group study was conducted including 50 subjects (mothers) lasting 4 months. Only healthy volunteers were included.

All subjects complied with all the following inclusion criteria: 1. Gestational age between 37 and not above 42 weeks, 2. Baby to be enrolled between birth and V1, 3. Mother not younger than 18 years and not older than 40 years of age, 4. pre-pregnancy BMI of the mother between 18.5-29.5. Mothers willing to breastfeed for the first 4 months after giving birth.

Subjects representing one or more of the following criteria are excluded from participation in the study: 1. Gestational diabetes, 2. HTA>140/90, 3. Mothers who are smokers while breast-feeding, 4. Subject who cannot be expected to comply with the study procedures. 5. Currently participating or having participated in another clinical trial during the last 12 weeks prior to the beginning of this study.

HMOs Sample Preparation and Analysis

HMOs analysis was conducted in duplicates on a 1 mL sample of whole breast milk, corresponding to a complete feed, and taken after 30, 60 and 120 days after infants' birth (post partum). 3'-Sialyllactose and 6'-Sialyllactose were recorded at several stages and up to 240 days after infants' birth Sample Preparation 1 mL of well mixed whole breast milk was centrifuged for 20 min at 1700×g. About 0.1 mL of skimmed milk supernatant was diluted 10× with water and 0.01 mL of the thus diluted supernatant were taken as a sample for analysis.

Analysis

Samples were analysed by high performance ion exchange chromatography (HPAEC; Thermo, Dionex, Ca) equipped with a CarboPac PA1 column (Thermo, Dionex, Ca) for separation and a pulsed amperometric detector (PAD) for detection of carbohydrates. Oligosaccharide identification was done based on comparison of retention times to authentic standards and enzymatic hydrolysis of samples (e.g. fucosidase, sialidase, galactosidase). Oligosaccharide quantification was done using external standard curves with pure authentic oligosaccharides.

Statistical Methods

Data collection points were 1, 2 and 4 months after infants' birth. Longitudinal analysis was carried out using linear mixed models. Adjusted R-squares are computed to obtain the degree of variability that is explained by the statistical models used. Where appropriate P-values for testing differences between genders and time points have been computed.

Analysis of concentrations of HMOs was carried out using a mixed-effects linear model:

$$\text{Conc.} = \text{Age} + \text{Age}^2 + \text{Gender} + \text{Age}*\text{Gender} + (\text{Age}^2)*\text{Gender} + \text{Random Effects}.$$

Random effects are subject specific terms to model the underlying correlation between repeat measures. If necessary higher order terms in Age were examined.

Results

The results of the study are shown in FIGS. 1 to 6. In FIGS. 2 to 6, V1, V2 and V3 determine post partum days 30, 60 and 120, respectively.

Figure 1B:
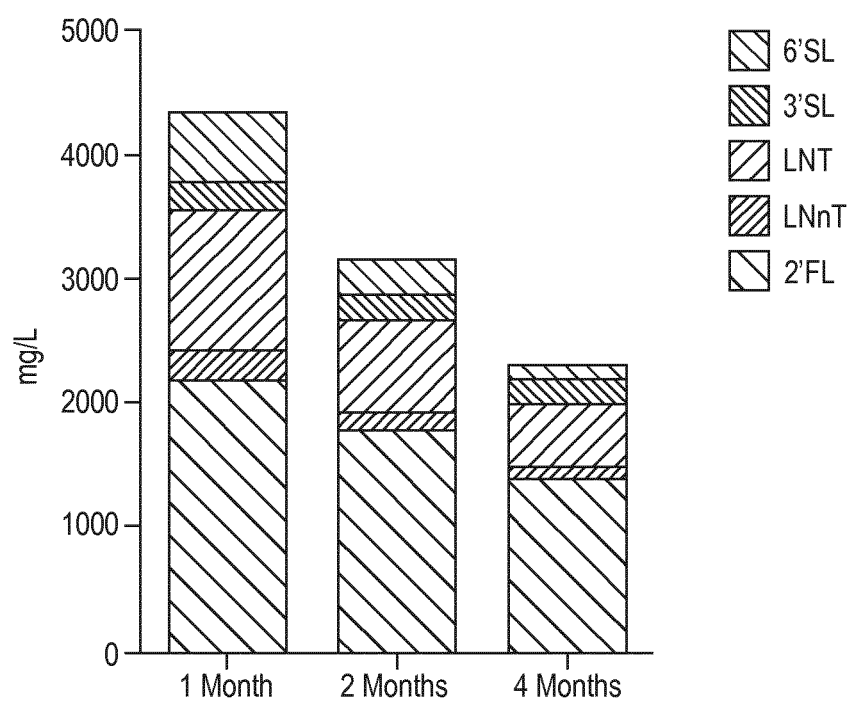
FIG. 1B depicts the evolving concentration of HMOs in mg/L of human milk over time.

As can be seen from FIG. 1A and FIG. 1B, the absolute HMOs concentration in human breast milk decreases with time as determined after 30, 60 and 120 days after infants' birth. In FIG. 1A the HMOs concentrations were calculated from all samples including those with very low 2'FL levels (<100 mg/L, which are presumed non-secretors). In FIG. 1B the HMOs concentrations were calculated from samples comprising 2'Fucosyllactose (2'FL)>100 mg/L.

FIGS. 1 to 6 further demonstrate that also the individual concentrations of 2'Fucosyllactose, 3'Sialyllactose, 6'Sialyllactose, Lacto-N-neotetraose, Lacto-N-tetraose decrease within 30, 60 and 120 days after infants' birth.

In addition, it was also found that the weight ratio of 3'-Sialyllactose and 6'-Sialyllactose in human breast milk increases with time as determined after 11, 30, 60, 120 and 240 days after infants' birth. While at the very beginning of the lactation period the 3'SL/6'SL ratio is about 1.53:10 with 6'SL as the major portion of sialyllactose in human breast milk, said ratio shifts with time towards about 5.86:1 with 3'SL as the major portion of sialyllactose in human breast milk after 8 months post partum. Further, the mean weight ratio of 3'-Sialyllactose and 6'-Sialyllactose in human breast milk during the lactation period was found to be about 1:1.

CONCLUSION

Example 3 clearly demonstrates that the age-tailored nutritional composition system of the present invention provides HMOs in ranges matching closely the mother's milk physiological levels, and, in particular, takes into account the evolving nutritional needs of infants in at least the first 2 months of life of the infants.

Therefore, the nutritional composition system of the present invention was demonstrated to provide a suitable nutritional solution for reflecting the evolving nutritional needs of the infants over time and, in particular, mimic the evolving nutritional quality and composition of breast milk during the lactation period.

The invention claimed is:

1. A method for providing at least one health benefit to infants, the method comprising:
    administering an age-tailored nutritional composition system comprising at least one nutritional composition A and at least one nutritional composition B to the infants, the administering of the age-tailored nutritional composition system comprises administering the at least one nutritional composition A to an infant from 0 up to 1 month of age;
    the administering of the age-tailored nutritional composition system further comprises administering the at least one nutritional composition B to an infant above 1 month and up to 2 months of age;
    the nutritional compositions A and B each comprise human milk oligosaccharides (HMOs), and the nutritional composition A comprises the HMOs in an amount from 3590 to 3673 mg/L of the nutritional composition A, and the nutritional composition B comprises the HMOs in an amount from 2558 to 2602 mg/L of the nutritional composition B.

2. A method for providing nutrition to an infant, the method comprising:
    feeding an infant from 0 up to 1 month of age at least one nutritional composition A; and
    feeding an infant above 1 month and up to 2 months of age at least one nutritional composition B,
    wherein the nutritional compositions A and B comprise HMOs, and the nutritional composition A comprises the HMOs in an amount from 3590 to 3673 mg/L of the nutritional composition A, and the nutritional composition B comprises the HMOs in an amount from 2558 to 2602 mg/L of the nutritional composition B.

3. The method according to claim 2, further comprising:
    feeding an infant above 2 months and up to 4 months of age a nutritional composition C;
    the nutritional composition C comprises HMOs; and
    the nutritional compositions A, B and C differ from each other in the amount of the HMOs present therein.

4. The method according to claim 2, wherein feeding an infant from 0 up to 1 month of age at least one nutritional composition A comprises feeding two nutritional compositions A, wherein the two nutritional compositions A are selected from the group consisting of:
    a first nutritional composition A1 for infants from 0 up to 7 days of age, and a second nutritional composition A2 for infants from 8 days up to 1 month of age;
    a first nutritional composition A1 for infants from 0 up to 6 days of age, and a second nutritional composition A2 for infants from 7 days up to 1 month of age;
    a first nutritional composition A1 for infants from 0 up to 5 days of age, and a second nutritional composition A2 for infants from 6 days up to 1 month of age;
    a first nutritional composition A1 for infants from 0 up to 4 days of age, and a second nutritional composition A2 for infants from 5 days up to 1 month of age; and
    a first nutritional composition A1 for infants from 0 up to 3 days of age, and a second nutritional composition A2 for infants from 4 days up to 1 month of age.

5. The method according to claim 1, wherein the age-tailored nutritional composition system further comprises at least one nutritional composition C, and the administering of the age-tailored nutritional composition system further comprises administering the at least one nutritional composition C to an infant above 2 months and up to 4 months of age.

6. The method according to claim 1, wherein the amounts of the HMOs present in each of the nutritional compositions A and B are selected according to the age of the infants.

7. The method according to claim 5, wherein the amount of the HMOs present in the at least one nutritional composition B exceeds the amount of the HMOs present in the at least one nutritional composition C.

8. The method according to claim 5, wherein the nutritional composition C comprises the HMOs in an amount from 500 to 2500 mg/L of the nutritional composition C.

9. The method according to claim 1, wherein the at least one nutritional composition A comprises a first nutritional composition A1 and a second nutritional composition A2, and the method comprises a step selected from the group consisting of:

administering the first nutritional composition A1 to an infant from 0 up to 7 days of age, and administering the second nutritional composition A2 to an infant from 8 days up to 1 month of age;

administering the first nutritional composition A1 to an infant from 0 up to 6 days of age, and administering the second nutritional composition A2 to an infant from 7 days up to 1 month of age;

administering the first nutritional composition A1 to an infant from 0 up to 5 days of age, and administering the second nutritional composition A2 to an infant from 6 days up to 1 month of age;

administering the first nutritional composition A1 to an infant from 0 up to 4 days of age, and administering the second nutritional composition A2 to an infant from 5 days up to 1 month of age; and administering the first nutritional composition A1 to an infant from 0 up to 3 days of age, and administering the second nutritional composition A2 to an infant from 4 days up to 1 month of age.

10. The method according to claim 1, wherein the HMOs are selected from HMOs which are naturally present in human breast milk.

11. The method according to claim 1, wherein the HMOs are selected from the group consisting of 2'Fucosyllactose, 3' Sialyllactose, 6'Sialyllactose, Lacto-N-neotetraose, Lacto-N-tetraose, and combinations thereof.

12. The method according to claim 1, wherein the HMOs comprise 2'Fucosyllactose, 3' Sialyllactose, 6' Sialyllactose, Lacto-N-neotetraose, and Lacto-N-tetraose individually in each of the nutritional compositions A and B in an amount from 280 to 350 mg/L of the corresponding nutritional composition.

13. The method according to claim 5, wherein the age-tailored nutritional composition system comprises at least one formulation selected from the group consisting of:

2'Fucosyllactose is present in the nutritional composition A in an amount from 1450 to 1520 mg/L of the nutritional composition A, the nutritional composition B in an amount from 1200 to 1210 mg/L of the nutritional composition B, and the nutritional composition C in an amount from 920 to 980 mg/L of the nutritional composition C;

3'Sialyllactose is present in the nutritional composition A in an amount from 225 to 240 mg/L of the nutritional composition A, the nutritional composition B in an amount from 200 to 225 mg/L of the nutritional composition B, and the nutritional composition C in an amount from 200 to 210 mg/L of the nutritional composition C;

6'Sialyllactose is present in the nutritional composition A in an amount from 530 to 550 mg/L of the nutritional composition A, the nutritional composition B in an amount from 270 to 280 mg/L of the nutritional composition B, and the nutritional composition C in an amount from 125 to 135 mg/L of the composition;

Lacto-N-neotetraose is present in the nutritional composition A in an amount from 220 to 255 mg/L of the nutritional composition A, the nutritional composition B in an amount from 130 to 165 mg/L of the nutritional composition B, and the nutritional composition C in an amount from 80 to 110 mg/L of the nutritional composition C; and Lacto-N-tetraose is present in the nutritional composition A in an amount from 1060 to 1215 mg/L of the nutritional composition A, the nutritional composition B in an amount from 730 to 750 mg/L of the nutritional composition B, and the nutritional composition C in an amount from 490 to 515 mg/L of the nutritional composition C.

14. The method according to claim 1, wherein the nutritional compositions A and B are infant formulae.

15. The method according to claim 1, wherein the nutritional compositions A and B are packed in single dose units.

* * * * *